US012600759B2

(12) United States Patent
Adak et al.

(10) Patent No.: US 12,600,759 B2
(45) Date of Patent: Apr. 14, 2026

(54) PROCESS OF PREPARATION OF GLUCAGON-LIKE PEPTIDE-1 (GLP-1) RECEPTOR AGONISTS AND THEIR ANALOGS

(71) Applicant: ENZENE BIOSCIENCES LIMITED, Pune Maharashtra (IN)

(72) Inventors: Sandip Adak, Pune Maharashtra (IN); Manoj Bonte, Pune Maharashtra (IN); Chandrakant Kulkarni, Pune Maharashtra (IN); Swamy Veeranarayana, Pune Maharashtra (IN); Nivrutti Jogdand, Pune Maharashtra (IN)

(73) Assignee: ENZENE BIOSCIENCES LIMITED, Pune Maharashtra (IN)

( * ) Notice: Subject to any disclaimer, the term of this patent is extended or adjusted under 35 U.S.C. 154(b) by 940 days.

(21) Appl. No.: 17/440,127

(22) PCT Filed: Mar. 19, 2020

(86) PCT No.: PCT/IB2020/052504
§ 371 (c)(1),
(2) Date: Sep. 16, 2021

(87) PCT Pub. No.: WO2020/188510
PCT Pub. Date: Sep. 24, 2020

(65) Prior Publication Data
US 2022/0153804 A1 May 19, 2022

(30) Foreign Application Priority Data

Mar. 19, 2019  (IN) .............................. 201921010752
Apr. 12, 2019  (IN) .............................. 201921014929

(51) Int. Cl.
C07K 1/10     (2006.01)
C07K 1/06     (2006.01)
C07K 14/605   (2006.01)

(52) U.S. Cl.
CPC ............ *C07K 14/605* (2013.01); *C07K 1/061* (2013.01); *C07K 1/10* (2013.01)

(58) Field of Classification Search
CPC ........ C07K 14/605; C07K 1/061; C07K 1/10; C07K 5/06095; C07K 5/06104; C07K 1/14; A61K 38/00; A61P 3/10
See application file for complete search history.

(56) References Cited

FOREIGN PATENT DOCUMENTS

| | | | |
|---|---|---|---|
| CN | 108059666 B | 9/2018 | |
| CN | 109180801 A * | 1/2019 | ........... C07K 14/605 |
| WO | 2010046900 A2 | 4/2010 | |
| WO | 2018104922 A1 | 6/2018 | |

OTHER PUBLICATIONS

Bycroft et al, J. Chem. Soc., Chem. Commun., 1993, 778-779 (Year: 1993).*
Spivey et al, Annu. Rep. Prog. Chem., Sect. B, 1999, 95, 83-95 (Year: 1999).*
International Application No. PCT/IB2020/052504, International Search Report mailed Dec. 7, 2020, 3 pages.

* cited by examiner

*Primary Examiner* — Sudhakar Katakam
(74) *Attorney, Agent, or Firm* — COZEN O'CONNOR

(57) ABSTRACT

The present invention relates to the processes for preparing glucagon-like peptide-1 (glp-1) receptor agonists and their analogs. The present invention further relates to processes for preparing liraglutide, D-liraglutide, semaglutide and D-semaglutide. The present invention specifically relates to processes for preparing glucagon-like peptide-1 (glp-1) agonist and their analogs, wherein the liraglutide, D-liraglutide, semaglutide and D-semaglutide produced are substantially pure. The present invention also relates to preparation of glucagon-like peptide-1 (glp-1) agonist and their analogs by solid and solution phase method.

4 Claims, 8 Drawing Sheets

Specification includes a Sequence Listing.

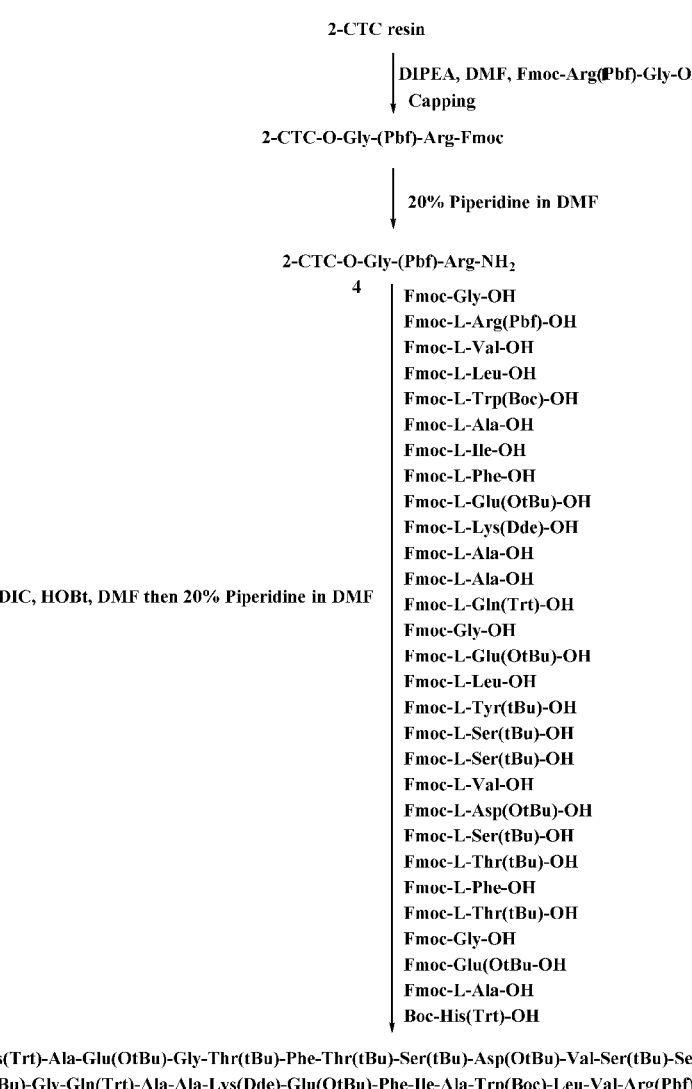

2-CTC resin

DIPEA, DMF, Fmoc-Arg(Pbf)-Gly-OH
Capping

2-CTC-O-Gly-(Pbf)-Arg-Fmoc

20% Piperidine in DMF

2-CTC-O-Gly-(Pbf)-Arg-NH$_2$
4

DIC, HOBt, DMF then 20% Piperidine in DMF

Fmoc-Gly-OH
Fmoc-L-Arg(Pbf)-OH
Fmoc-L-Val-OH
Fmoc-L-Leu-OH
Fmoc-L-Trp(Boc)-OH
Fmoc-L-Ala-OH
Fmoc-L-Ile-OH
Fmoc-L-Phe-OH
Fmoc-L-Glu(OtBu)-OH
Fmoc-L-Lys(Dde)-OH
Fmoc-L-Ala-OH
Fmoc-L-Ala-OH
Fmoc-L-Gln(Trt)-OH
Fmoc-Gly-OH
Fmoc-L-Glu(OtBu)-OH
Fmoc-L-Leu-OH
Fmoc-L-Tyr(tBu)-OH
Fmoc-L-Ser(tBu)-OH
Fmoc-L-Ser(tBu)-OH
Fmoc-L-Val-OH
Fmoc-L-Asp(OtBu)-OH
Fmoc-L-Ser(tBu)-OH
Fmoc-L-Thr(tBu)-OH
Fmoc-L-Phe-OH
Fmoc-L-Thr(tBu)-OH
Fmoc-Gly-OH
Fmoc-Glu(OtBu-OH
Fmoc-L-Ala-OH
Boc-His(Trt)-OH Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Dde)-Glu(OtBu)-Phe-Ile-Ala-Trp(Boc)-Leu-Val-Arg(Pbf)-Gly-Arg(Pbf)-Gly-O-2-CTC

6

3% Hydrazine hydrate

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(NH$_2$)-Glu(OtBu)-Phe-Ile-Ala-Trp(Boc)-Leu-Val-Arg(Pbf)-Gly-Arg(Pbf)-Gly-O-2-CTC

7

1. Fmoc-Glu-OtBu
2. Palmitic acid

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Glu-OtBu-Palmitoyl)-Glu(OtBu)-Phe-Ile-Ala-Trp(Boc)-Leu-Val-Arg(Pbf)-Gly-Arg(Pbf)-Gly-O-2-CTC

8

TFA:TIS:DODT:Water

His-Ala-Glu-Gly-Thr-Phe-Thr-Ser-Asp-Val-Ser-Ser-Tyr-Leu-Glu-Gly-Gln-Ala-Ala-Lys(Glu-Palmitoyl)-Glu-Phe-Ile-Ala-Trp-Leu-Val-Arg-Gly-Arg-Gly-OH     Crude Liraglutide

9

Purification & Lyophilization

Pure Liraglutide

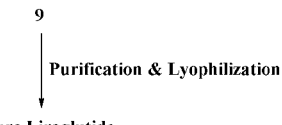

Figure.1

2-CTC resin

| DIPEA, DMF, Fmoc-Arg(Pbf)-Gly-OH
↓ Capping

2-CTC-O-Gly-(Pbf)-Arg-Fmoc

| 20% Piperidine in DMF

2-CTC-O-Gly-(Pbf)-Arg-NH$_2$
4

DIC, HOBt, DMF then 20% Piperidine in DMF

Fmoc-L-Arg(Pbf)-Gly-OH
Fmoc-L-Val-OH
Fmoc-L-Leu-OH
Fmoc-L-Trp(Boc)-OH
Fmoc-L-Ala-OH
Fmoc-L-Ile-OH
Fmoc-L-Phe-OH
Fmoc-L-Glu(OtBu)-OH
Fmoc-L-Lys(Dde)-OH
Fmoc-L-Ala-OH
Fmoc-L-Ala-OH
Fmoc-L-Gln(Trt)-OH
Fmoc-L-Glu(OtBu)-Gly-OH
Fmoc-L-Leu-OH
Fmoc-L-Tyr(tBu)-OH
Fmoc-L-Ser(tBu)-OH
Fmoc-L-Ser(tBu)-OH
Fmoc-L-Val-OH
Fmoc-L-Asp(OtBu)-OH
Fmoc-L-Ser(tBu)-OH
Fmoc-L-Thr(tBu)-OH
Fmoc-L-Phe-OH
Fmoc-L-Thr(tBu)-OH
Fmoc-L-Glu(OtBu)-Gly-OH
Fmoc-L-Ala-OH
Boc-L-His(Trt)-OH Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-
Glu(OtBu)-Gly-Gln(Trt)-Ala-Ala-Lys(Dde)-Glu(OtBu)-Phe-Ile-Ala-Trp(Boc)-Leu-Val-Arg(Pbf)-Gly-Arg(Pbf)-Gly-O-2-CTC
6

| 3% Hydrazine hydrate

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-
Glu(OtBu)-Gly-Gln(Trt)-Ala-Ala-Lys(NH$_2$)-Glu(OtBu)-Phe-Ile-Ala-Trp(Boc)-Leu-Val-Arg(Pbf)-Gly-Arg(Pbf)-Gly-O-2-CTC
7

| 1. Fmoc-Glu-OtBu
| 2. Palmitic acid

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-
Gly-Gln(Trt)-Ala-Ala-Lys(Glu-OtBu-Palmitoyl)-Glu(OtBu)-Phe-Ile-Ala-Trp(Boc)-Leu-Val-Arg(Pbf)-Gly-Arg(Pbf)-Gly-O-2-CTC
8

| TFA:TIS:DODT:Water

His-Ala-Glu-Gly-Thr-Phe-Thr-Ser-Asp-Val-Ser-Ser-Tyr-Leu-Glu-Gly-Gln-Ala-
Ala-Lys(Glu-Palmitoyl)-Glu-Phe-Ile-Ala-Trp-Leu-Val-Arg-Gly-Arg-Gly-OH
Crude Liraglutide
9

| Purification & Lyophilization

Pure Liraglutide

Figure.2

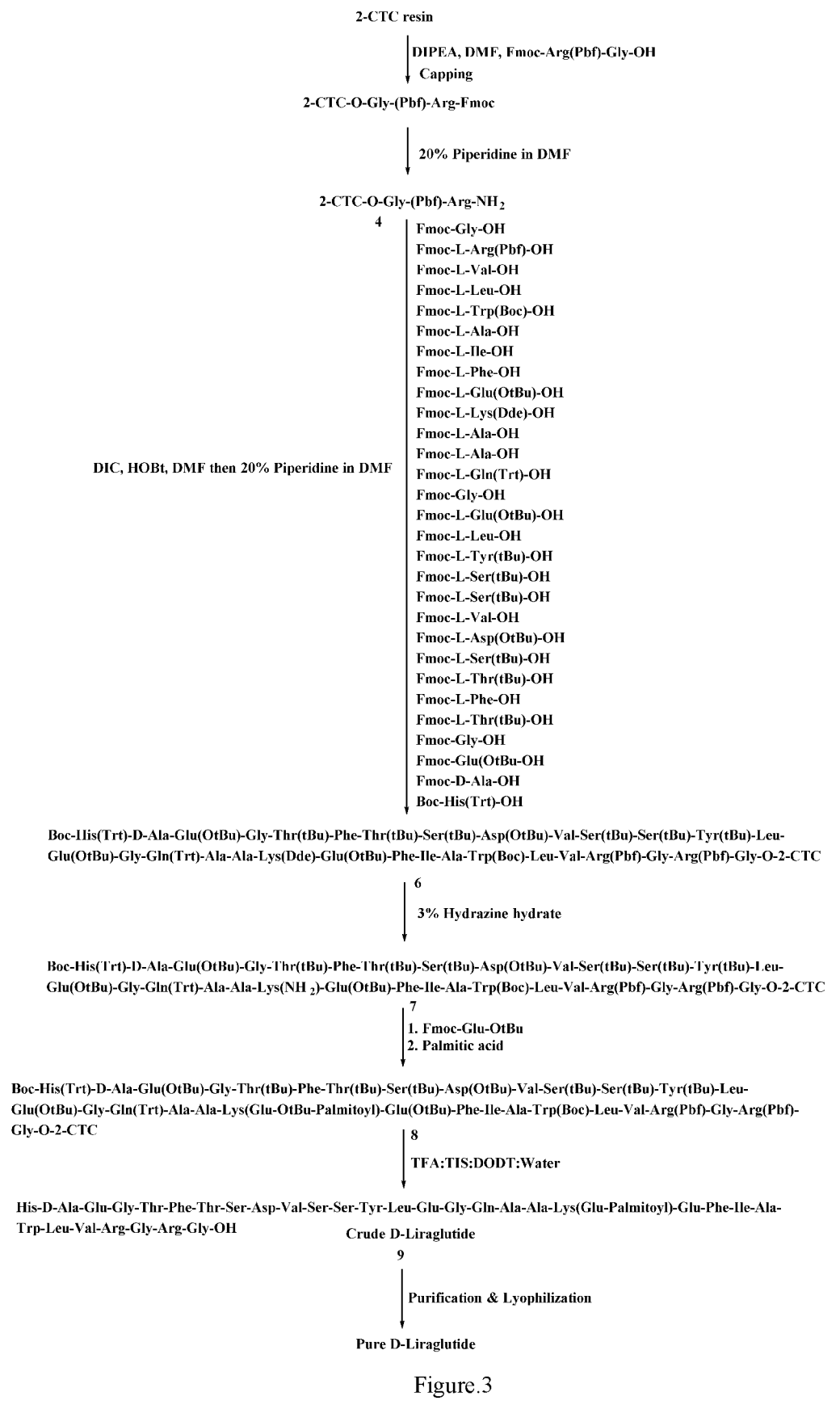

2-CTC resin

| DIPEA, DMF, Fmoc-Arg(Pbf)-Gly-OH
↓ Capping

2-CTC-O-Gly-(Pbf)-Arg-Fmoc

| 20% Piperidine in DMF
↓

2-CTC-O-Gly-(Pbf)-Arg-NH$_2$

4

DIC, HOBt, DMF then 20% Piperidine in DMF

Fmoc-Gly-OH
Fmoc-L-Arg(Pbf)-OH
Fmoc-L-Val-OH
Fmoc-L-Leu-OH
Fmoc-L-Trp(Boc)-OH
Fmoc-L-Ala-OH
Fmoc-L-Ile-OH
Fmoc-L-Phe-OH
Fmoc-L-Glu(OtBu)-OH
Fmoc-L-Lys(Dde)-OH
Fmoc-L-Ala-OH
Fmoc-L-Ala-OH
Fmoc-L-Gln(Trt)-OH
Fmoc-Gly-OH
Fmoc-L-Glu(OtBu)-OH
Fmoc-L-Leu-OH
Fmoc-L-Tyr(tBu)-OH
Fmoc-L-Ser(tBu)-OH
Fmoc-L-Ser(tBu)-OH
Fmoc-L-Val-OH
Fmoc-L-Asp(OtBu)-OH
Fmoc-L-Ser(tBu)-OH
Fmoc-L-Thr(tBu)-OH
Fmoc-L-Phe-OH
Fmoc-L-Thr(tBu)-OH
Fmoc-Gly-OH
Fmoc-Glu(OtBu-OH
Fmoc-D-Ala-OH
Boc-His(Trt)-OH Boc-His(Trt)-D-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Dde)-Glu(OtBu)-Phe-Ile-Ala-Trp(Boc)-Leu-Val-Arg(Pbf)-Gly-Arg(Pbf)-Gly-O-2-CTC

6

| 3% Hydrazine hydrate
↓

Boc-His(Trt)-D-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(NH$_2$)-Glu(OtBu)-Phe-Ile-Ala-Trp(Boc)-Leu-Val-Arg(Pbf)-Gly-Arg(Pbf)-Gly-O-2-CTC

7

1. Fmoc-Glu-OtBu
2. Palmitic acid

Boc-His(Trt)-D-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Glu-OtBu-Palmitoyl)-Glu(OtBu)-Phe-Ile-Ala-Trp(Boc)-Leu-Val-Arg(Pbf)-Gly-Arg(Pbf)-Gly-O-2-CTC

8

| TFA:TIS:DODT:Water
↓

His-D-Ala-Glu-Gly-Thr-Phe-Thr-Ser-Asp-Val-Ser-Ser-Tyr-Leu-Glu-Gly-Gln-Ala-Ala-Lys(Glu-Palmitoyl)-Glu-Phe-Ile-Ala-Trp-Leu-Val-Arg-Gly-Arg-Gly-OH Crude D-Liraglutide

9

| Purification & Lyophilization
↓

Pure D-Liraglutide

Figure.3

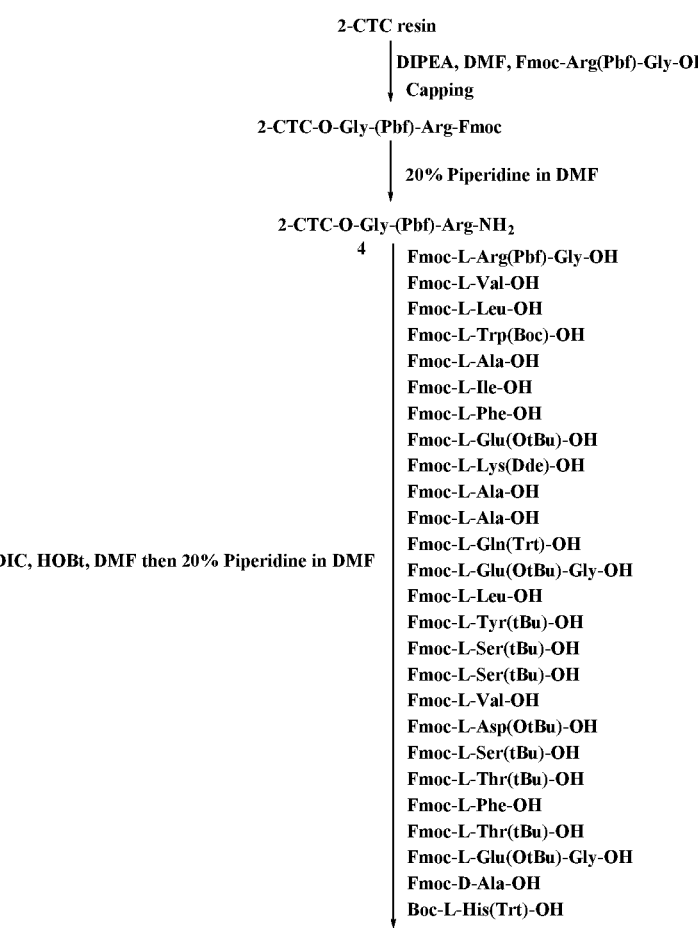

2-CTC resin

DIPEA, DMF, Fmoc-Arg(Pbf)-Gly-OH
   Capping

2-CTC-O-Gly-(Pbf)-Arg-Fmoc

20% Piperidine in DMF

2-CTC-O-Gly-(Pbf)-Arg-NH$_2$
4

Fmoc-L-Arg(Pbf)-Gly-OH
Fmoc-L-Val-OH
Fmoc-L-Leu-OH
Fmoc-L-Trp(Boc)-OH
Fmoc-L-Ala-OH
Fmoc-L-Ile-OH
Fmoc-L-Phe-OH
Fmoc-L-Glu(OtBu)-OH
Fmoc-L-Lys(Dde)-OH
Fmoc-L-Ala-OH
Fmoc-L-Ala-OH
Fmoc-L-Gln(Trt)-OH
Fmoc-L-Glu(OtBu)-Gly-OH
Fmoc-L-Leu-OH
Fmoc-L-Tyr(tBu)-OH
Fmoc-L-Ser(tBu)-OH
Fmoc-L-Ser(tBu)-OH
Fmoc-L-Val-OH
Fmoc-L-Asp(OtBu)-OH
Fmoc-L-Ser(tBu)-OH
Fmoc-L-Thr(tBu)-OH
Fmoc-L-Phe-OH
Fmoc-L-Thr(tBu)-OH
Fmoc-L-Glu(OtBu)-Gly-OH
Fmoc-D-Ala-OH
Boc-L-His(Trt)-OH DIC, HOBt, DMF then 20% Piperidine in DMF Boc-His(Trt)-D-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Dde)-Glu(OtBu)-Phe-Ile-Ala-Trp(Boc)-Leu-Val-Arg(Pbf)-Gly-Arg(Pbf)-Gly-O-2-CTC
6

3% Hydrazine hydrate

Boc-His(Trt)-D-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(NH$_2$)-Glu(OtBu)-Phe-Ile-Ala-Trp(Boc)-Leu-Val-Arg(Pbf)-Gly-Arg(Pbf)-Gly-O-2-CTC
7

1. Fmoc-Glu-OtBu
   2. Palmitic acid

Boc-His(Trt)-D-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Glu-OtBu-Palmitoyl)-Glu(OtBu)-Phe-Ile-Ala-Trp(Boc)-Leu-Val-Arg(Pbf)-Gly-Arg(Pbf)-Gly-O-2-CTC
8

TFA:TIS:DODT:Water

His-D-Ala-Glu-Gly-Thr-Phe-Thr-Ser-Asp-Val-Ser-Ser-Tyr-Leu-Glu-Gly-Gln-Ala-Ala-Lys(Glu-Palmitoyl)-Glu-Phe-Ile-Ala-Trp-Leu-Val-Arg-Gly-Arg-Gly-OH
Crude D-Liraglutide
9

Purification & Lyophilization

Pure D-Liraglutide

Figure.4

2-CTC resin

| DIPEA, DMF, Fmoc-Arg(Pbf)-Gly-OH
↓ Capping

2-CTC-O-Gly-(Pbf)-Arg-Fmoc

| 20% Piperidine in DMF
↓

2-CTC-O-Gly-(Pbf)-Arg-NH$_2$

4

DIC, HOBt, DMF then 20% Piperidine in DMF

Fmoc-Gly-OH
Fmoc-L-Arg(Pbf)-OH
Fmoc-L-Val-OH
Fmoc-L-Leu-OH
Fmoc-L-Trp(Boc)-OH
Fmoc-L-Ala-OH
Fmoc-L-Ile-OH
Fmoc-L-Phe-OH
Fmoc-L-Glu(OtBu)-OH
Fmoc-L-Lys(Dde)-OH
Fmoc-L-Ala-OH
Fmoc-L-Ala-OH
Fmoc-L-Gln(Trt)-OH
Fmoc-Gly-OH
Fmoc-L-Glu(OtBu)-OH
Fmoc-L-Leu-OH
Fmoc-L-Tyr(tBu)-OH
Fmoc-L-Ser(tBu)-OH
Fmoc-L-Ser(tBu)-OH
Fmoc-L-Val-OH
Fmoc-L-Asp(OtBu)-OH
Fmoc-L-Ser(tBu)-OH
Fmoc-L-Thr(tBu)-OH
Fmoc-L-Phe-OH
Fmoc-L-Thr(tBu)-OH
Fmoc-Gly-OH
Fmoc-L-Glu(OtBu)-OH
Fmoc-L-Ala-OH
Boc-L-His(Trt)-OH Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Dde)-Glu(OtBu)-Phe-Ile-Ala-Trp(Boc)-Leu-Val-Arg(Pbf)-Gly-Arg(Pbf)-Gly-O-2-CTC

6

| 3% Hydrazine hydrate
↓

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(NH$_2$)-Glu(OtBu)-Phe-Ile-Ala-Trp(Boc)-Leu-Val-Arg(Pbf)-Gly-Arg(Pbf)-Gly-O-2-CTC

7

1. Fmoc-PEG2-CH$_2$-COOH
2. Fmoc-PEG2-CH$_2$-COOH
3. Fmoc-Glu-OtBu
4. 18-tBu-18-Oxaoctadecanoicacid Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys[PEG2-PEG2-Glu-OtBu-18-tBu-oxooctadecanoyl]-Glu(OtBu)-Phe-Ile-Ala-Trp(Boc)-Leu-Val-Arg(Pbf)-Gly-Arg(Pbf)-Gly-O-2-CTC          8

| TFA:TIS:DODT:Water
↓

His-Ala-Glu-Gly-Thr-Phe-Thr-Ser-Asp-Val-Ser-Ser-Tyr-Leu-Glu-Gly-Gln-Ala-Ala-Lys[PEG2-PEG2-Glu-18-oxooctadecanoyl]-Glu-Phe-Ile-Ala-Trp-Leu-Val-Arg-Gly-Arg-Gly-OH Crude Semaglutide

9

| Purification & Lyophilization
↓

Pure Semaglutide

Figure.5

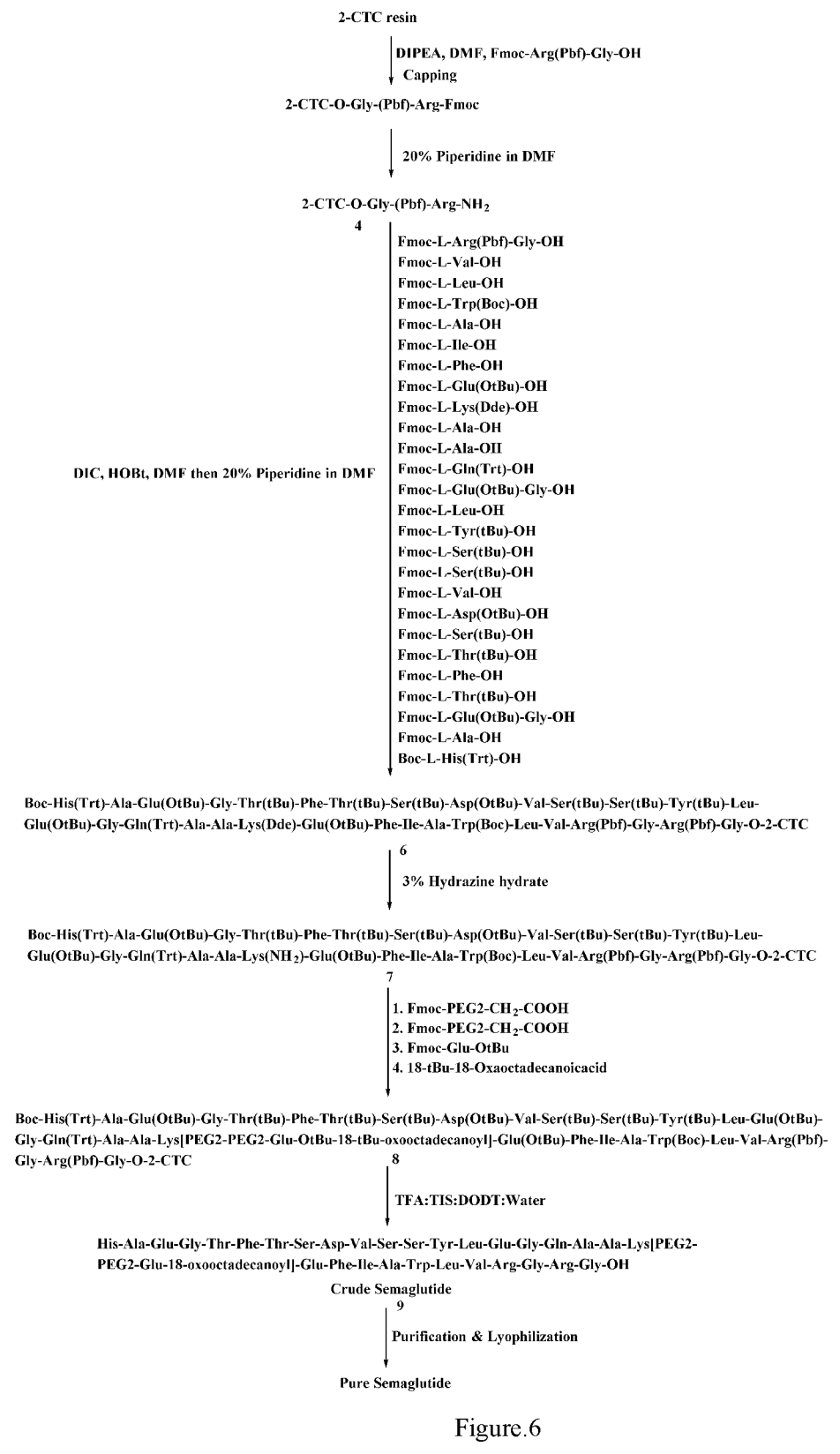

2-CTC resin

| DIPEA, DMF, Fmoc-Arg(Pbf)-Gly-OH
↓ Capping

2-CTC-O-Gly-(Pbf)-Arg-Fmoc

| 20% Piperidine in DMF
↓

2-CTC-O-Gly-(Pbf)-Arg-NH₂

4

DIC, HOBt, DMF then 20% Piperidine in DMF |

Fmoc-L-Arg(Pbf)-Gly-OH
Fmoc-L-Val-OH
Fmoc-L-Leu-OH
Fmoc-L-Trp(Boc)-OH
Fmoc-L-Ala-OH
Fmoc-L-Ile-OH
Fmoc-L-Phe-OH
Fmoc-L-Glu(OtBu)-OH
Fmoc-L-Lys(Dde)-OH
Fmoc-L-Ala-OH
Fmoc-L-Ala-OH
Fmoc-L-Gln(Trt)-OH
Fmoc-L-Glu(OtBu)-Gly-OH
Fmoc-L-Leu-OH
Fmoc-L-Tyr(tBu)-OH
Fmoc-L-Ser(tBu)-OH
Fmoc-L-Ser(tBu)-OH
Fmoc-L-Val-OH
Fmoc-L-Asp(OtBu)-OH
Fmoc-L-Ser(tBu)-OH
Fmoc-L-Thr(tBu)-OH
Fmoc-L-Phe-OH
Fmoc-L-Thr(tBu)-OH
Fmoc-L-Glu(OtBu)-Gly-OH
Fmoc-L-Ala-OH
Boc-L-His(Trt)-OH Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-
Glu(OtBu)-Gly-Gln(Trt)-Ala-Ala-Lys(Dde)-Glu(OtBu)-Phe-Ile-Ala-Trp(Boc)-Leu-Val-Arg(Pbf)-Gly-Arg(Pbf)-Gly-O-2-CTC

6

| 3% Hydrazine hydrate
↓

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-
Glu(OtBu)-Gly-Gln(Trt)-Ala-Ala-Lys(NH₂)-Glu(OtBu)-Phe-Ile-Ala-Trp(Boc)-Leu-Val-Arg(Pbf)-Gly-Arg(Pbf)-Gly-O-2-CTC

7

1. Fmoc-PEG2-CH₂-COOH
2. Fmoc-PEG2-CH₂-COOH
3. Fmoc-Glu-OtBu
4. 18-tBu-18-Oxaoctadecanoicacid Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-
Gly-Gln(Trt)-Ala-Ala-Lys[PEG2-PEG2-Glu-OtBu-18-tBu-oxooctadecanoyl]-Glu(OtBu)-Phe-Ile-Ala-Trp(Boc)-Leu-Val-Arg(Pbf)-
Gly-Arg(Pbf)-Gly-O-2-CTC        8

| TFA:TIS:DODT:Water
↓

His-Ala-Glu-Gly-Thr-Phe-Thr-Ser-Asp-Val-Ser-Ser-Tyr-Leu-Glu-Gly-Gln-Ala-Ala-Lys[PEG2-
PEG2-Glu-18-oxooctadecanoyl]-Glu-Phe-Ile-Ala-Trp-Leu-Val-Arg-Gly-Arg-Gly-OH Crude Semaglutide

9

| Purification & Lyophilization
↓

Pure Semaglutide

Figure.6

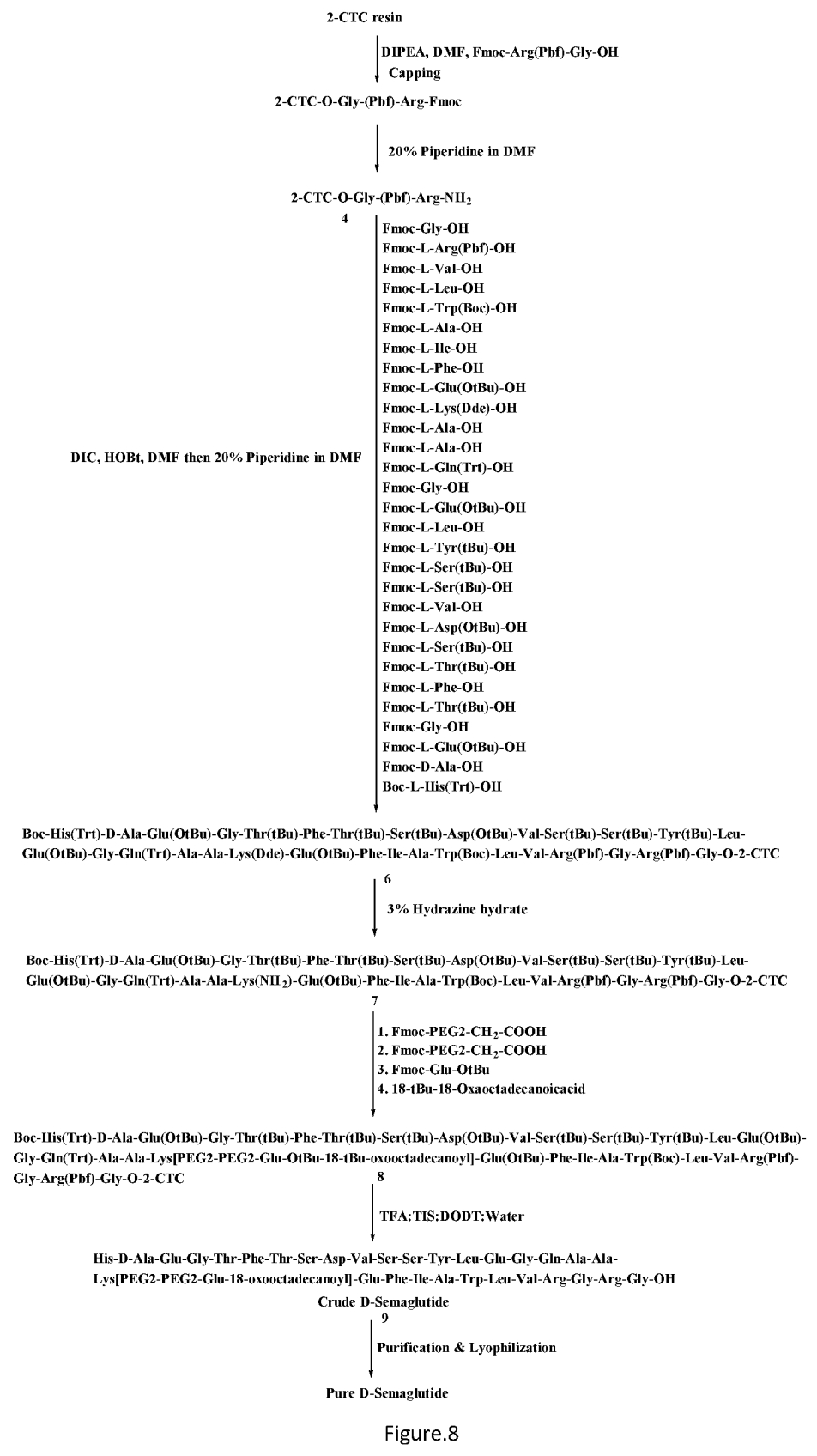

2-CTC resin

| DIPEA, DMF, Fmoc-Arg(Pbf)-Gly-OH
| Capping

2-CTC-O-Gly-(Pbf)-Arg-Fmoc

| 20% Piperidine in DMF

2-CTC-O-Gly-(Pbf)-Arg-NH$_2$

4

DIC, HOBt, DMF then 20% Piperidine in DMF

Fmoc-Gly-OH
Fmoc-L-Arg(Pbf)-OH
Fmoc-L-Val-OH
Fmoc-L-Leu-OH
Fmoc-L-Trp(Boc)-OH
Fmoc-L-Ala-OH
Fmoc-L-Ile-OH
Fmoc-L-Phe-OH
Fmoc-L-Glu(OtBu)-OH
Fmoc-L-Lys(Dde)-OH
Fmoc-L-Ala-OH
Fmoc-L-Ala-OH
Fmoc-L-Gln(Trt)-OH
Fmoc-Gly-OH
Fmoc-L-Glu(OtBu)-OH
Fmoc-L-Leu-OH
Fmoc-L-Tyr(tBu)-OH
Fmoc-L-Ser(tBu)-OH
Fmoc-L-Ser(tBu)-OH
Fmoc-L-Val-OH
Fmoc-L-Asp(OtBu)-OH
Fmoc-L-Ser(tBu)-OH
Fmoc-L-Thr(tBu)-OH
Fmoc-L-Phe-OH
Fmoc-L-Thr(tBu)-OH
Fmoc-Gly-OH
Fmoc-L-Glu(OtBu)-OH
Fmoc-D-Ala-OH
Boc-L-His(Trt)-OH Boc-His(Trt)-D-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Dde)-Glu(OtBu)-Phe-Ile-Ala-Trp(Boc)-Leu-Val-Arg(Pbf)-Gly-Arg(Pbf)-Gly-O-2-CTC

6

| 3% Hydrazine hydrate

Boc-His(Trt)-D-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(NH$_2$)-Glu(OtBu)-Phe-Ile-Ala-Trp(Boc)-Leu-Val-Arg(Pbf)-Gly-Arg(Pbf)-Gly-O-2-CTC

7

1. Fmoc-PEG2-CH$_2$-COOH
2. Fmoc-PEG2-CH$_2$-COOH
3. Fmoc-Glu-OtBu
4. 18-tBu-18-Oxaoctadecanoicacid Boc-His(Trt)-D-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys[PEG2-PEG2-Glu-OtBu-18-tBu-oxooctadecanoyl]-Glu(OtBu)-Phe-Ile-Ala-Trp(Boc)-Leu-Val-Arg(Pbf)-Gly-Arg(Pbf)-Gly-O-2-CTC

8

| TFA:TIS:DODT:Water

His-D-Ala-Glu-Gly-Thr-Phe-Thr-Ser-Asp-Val-Ser-Ser-Tyr-Leu-Glu-Gly-Gln-Ala-Ala-Lys[PEG2-PEG2-Glu-18-oxooctadecanoyl]-Glu-Phe-Ile-Ala-Trp-Leu-Val-Arg-Gly-Arg-Gly-OH Crude D-Semaglutide

9

| Purification & Lyophilization

Pure D-Semaglutide

Figure.8

SEQUENCE LISTING

```
<160> NUMBER OF SEQ ID NOS: 12

<210> SEQ ID NO 1
<211> LENGTH: 31
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: H-His
<220> FEATURE:
<221> NAME/KEY: MOD_RES
<222> LOCATION: (20)..(20)
<223> OTHER INFORMATION: Lys(gamma-Glu-palmitoyl)
<220> FEATURE:
<221> NAME/KEY: MOD_RES
<222> LOCATION: (31)..(31)
<223> OTHER INFORMATION: Gly-OH

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

-continued

```
<210> SEQ ID NO 2
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: H-His
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (20)..(20)
<223> OTHER INFORMATION: Lys(gamma Glu plamitoyl)
<220> FEATURE:
<221> NAME/KEY: MOD_RES
<222> LOCATION: (31)..(31)
<223> OTHER INFORMATION: Gly-OH

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 3
<211> LENGTH: 31
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: H-His
<220> FEATURE:
<221> NAME/KEY: MOD_RES
<222> LOCATION: (20)..(20)
<223> OTHER INFORMATION: Lys(PEG2-PEG2-Glu-18oxooctadecanoyl)
<220> FEATURE:
<221> NAME/KEY: MOD_RES
<222> LOCATION: (31)..(31)
<223> OTHER INFORMATION: Gly-OH

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: H-HIS
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (20)..(20)
<223> OTHER INFORMATION: Lys(PEG2-PEG2-Glu-18oxooctadecanoyl)
```

```
<220> FEATURE:
<221> NAME/KEY: MOD_RES
<222> LOCATION: (31)..(31)
<223> OTHER INFORMATION: Gly-OH

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Boc-His(Trt)
<220> FEATURE:
<221> NAME/KEY: MOD_RES
<222> LOCATION: (3)..(3)
<223> OTHER INFORMATION: Glu(OtBu)
<220> FEATURE:
<221> NAME/KEY: MOD_RES
<222> LOCATION: (5)..(5)
<223> OTHER INFORMATION: Thr(tBu)
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Asp(OtBu)
<220> FEATURE:
<221> NAME/KEY: MOD_RES
<222> LOCATION: (11)..(11)
<223> OTHER INFORMATION: Ser(tBu)
<220> FEATURE:
<221> NAME/KEY: MOD_RES
<222> LOCATION: (12)..(12)
<223> OTHER INFORMATION: Ser(tBu)
<220> FEATURE:
<221> NAME/KEY: MOD_RES
<222> LOCATION: (13)..(13)
<223> OTHER INFORMATION: Tyr(tBu)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (17)..(17)
<223> OTHER INFORMATION: Gln(trt)
<220> FEATURE:
<221> NAME/KEY: MOD_RES
<222> LOCATION: (20)..(20)
<223> OTHER INFORMATION: Lys(Dde)
<220> FEATURE:
<221> NAME/KEY: MOD_RES
<222> LOCATION: (21)..(21)
<223> OTHER INFORMATION: Glu(OtBu)
<220> FEATURE:
<221> NAME/KEY: MOD_RES
<222> LOCATION: (25)..(25)
<223> OTHER INFORMATION: Trp(Boc)
<220> FEATURE:
<221> NAME/KEY: MOD_RES
<222> LOCATION: (28)..(28)
```

```
<223> OTHER INFORMATION: Arg(Pbf)
<220> FEATURE:
<221> NAME/KEY: MOD_RES
<222> LOCATION: (30)..(30)
<223> OTHER INFORMATION: Arg(Pbf)
<220> FEATURE:
<221> NAME/KEY: MOD_RES
<222> LOCATION: (31)..(31)
<223> OTHER INFORMATION: Gly-O-2-CTC

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Boc-His(Trt)
<220> FEATURE:
<221> NAME/KEY: MOD_RES
<222> LOCATION: (3)..(3)
<223> OTHER INFORMATION: Glu(OtBu)
<220> FEATURE:
<221> NAME/KEY: MOD_RES
<222> LOCATION: (5)..(5)
<223> OTHER INFORMATION: Thr(tBu)
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Asp(OtBu)
<220> FEATURE:
<221> NAME/KEY: MOD_RES
<222> LOCATION: (11)..(11)
<223> OTHER INFORMATION: Ser(tBu)
<220> FEATURE:
<221> NAME/KEY: MOD_RES
<222> LOCATION: (12)..(12)
<223> OTHER INFORMATION: Ser(tBu)
<220> FEATURE:
<221> NAME/KEY: MOD_RES
<222> LOCATION: (13)..(13)
<223> OTHER INFORMATION: Tyr(tBu)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (17)..(17)
<223> OTHER INFORMATION: Gln(Trt)
<220> FEATURE:
<221> NAME/KEY: MOD_RES
<222> LOCATION: (20)..(20)
<223> OTHER INFORMATION: Lys(NH2)
<220> FEATURE:
<221> NAME/KEY: MOD_RES
<222> LOCATION: (21)..(21)
<223> OTHER INFORMATION: Glu(OtBu)
<220> FEATURE:
<221> NAME/KEY: MOD_RES
```

```
<222> LOCATION: (25)..(25)
<223> OTHER INFORMATION: Trp(Boc)
<220> FEATURE:
<221> NAME/KEY: MOD_RES
<222> LOCATION: (28)..(28)
<223> OTHER INFORMATION: Arg(Pbf)
<220> FEATURE:
<221> NAME/KEY: MOD_RES
<222> LOCATION: (30)..(30)
<223> OTHER INFORMATION: Arg(Pbf)
<220> FEATURE:
<221> NAME/KEY: MOD_RES
<222> LOCATION: (31)..(31)
<223> OTHER INFORMATION: Gly-O-2-CTC

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Boc-His(Trt)
<220> FEATURE:
<221> NAME/KEY: MOD_RES
<222> LOCATION: (3)..(3)
<223> OTHER INFORMATION: Glu(OtBu)
<220> FEATURE:
<221> NAME/KEY: MOD_RES
<222> LOCATION: (5)..(5)
<223> OTHER INFORMATION: Thr(tBu)
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Asp(OtBu)
<220> FEATURE:
<221> NAME/KEY: MOD_RES
<222> LOCATION: (11)..(11)
<223> OTHER INFORMATION: Ser(tBu)
<220> FEATURE:
<221> NAME/KEY: MOD_RES
<222> LOCATION: (12)..(12)
<223> OTHER INFORMATION: Ser(tBu)
<220> FEATURE:
<221> NAME/KEY: MOD_RES
<222> LOCATION: (13)..(13)
<223> OTHER INFORMATION: Tyr(tBu)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (17)..(17)
<223> OTHER INFORMATION: Gln(Trt)
<220> FEATURE:
<221> NAME/KEY: MOD_RES
<222> LOCATION: (20)..(20)
<223> OTHER INFORMATION: Lys(Glu-OtBu-Palmitoyl)
<220> FEATURE:
```

-continued

```
<221> NAME/KEY: MOD_RES
<222> LOCATION: (21)..(21)
<223> OTHER INFORMATION: Glu(OtBu)
<220> FEATURE:
<221> NAME/KEY: MOD_RES
<222> LOCATION: (25)..(25)
<223> OTHER INFORMATION: Trp(Boc)
<220> FEATURE:
<221> NAME/KEY: MOD_RES
<222> LOCATION: (28)..(28)
<223> OTHER INFORMATION: Arg(Pbf)
<220> FEATURE:
<221> NAME/KEY: MOD_RES
<222> LOCATION: (30)..(30)
<223> OTHER INFORMATION: Arg(Pbf)
<220> FEATURE:
<221> NAME/KEY: MOD_RES
<222> LOCATION: (31)..(31)
<223> OTHER INFORMATION: Gly-O-2-CTC

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Boc-His(Trt)
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: Glu(OtBu)
<220> FEATURE:
<221> NAME/KEY: MOD_RES
<222> LOCATION: (5)..(5)
<223> OTHER INFORMATION: Thr(tBu)
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Asp(OtBu)
<220> FEATURE:
<221> NAME/KEY: MOD_RES
<222> LOCATION: (11)..(11)
<223> OTHER INFORMATION: Ser(tBu)
<220> FEATURE:
<221> NAME/KEY: MOD_RES
<222> LOCATION: (12)..(12)
<223> OTHER INFORMATION: Ser(tBu)
<220> FEATURE:
<221> NAME/KEY: MOD_RES
<222> LOCATION: (13)..(13)
<223> OTHER INFORMATION: Tyr(tBu)
<220> FEATURE:
<221> NAME/KEY: MOD_RES
<222> LOCATION: (15)..(15)
<223> OTHER INFORMATION: Glu(OtBu)
```

```
<220> FEATURE:
<221> NAME/KEY: MOD_RES
<222> LOCATION: (17)..(17)
<223> OTHER INFORMATION: Gln(Trt)
<220> FEATURE:
<221> NAME/KEY: MOD_RES
<222> LOCATION: (20)..(20)
<223> OTHER INFORMATION: Lys(Dde)
<220> FEATURE:
<221> NAME/KEY: MOD_RES
<222> LOCATION: (21)..(21)
<223> OTHER INFORMATION: Glu(OtBu)
<220> FEATURE:
<221> NAME/KEY: MOD_RES
<222> LOCATION: (25)..(25)
<223> OTHER INFORMATION: Trp(Boc)
<220> FEATURE:
<221> NAME/KEY: MOD_RES
<222> LOCATION: (28)..(28)
<223> OTHER INFORMATION: Arg(Pbf)
<220> FEATURE:
<221> NAME/KEY: MOD_RES
<222> LOCATION: (30)..(30)
<223> OTHER INFORMATION: Arg(Pbf)
<220> FEATURE:
<221> NAME/KEY: MOD_RES
<222> LOCATION: (31)..(31)
<223> OTHER INFORMATION: Gly-O-2-CTC

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Boc-His(Trt)
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: Glu(OtBu)
<220> FEATURE:
<221> NAME/KEY: MOD_RES
<222> LOCATION: (5)..(5)
<223> OTHER INFORMATION: Thr(tBu)
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Asp(OtBu)
<220> FEATURE:
<221> NAME/KEY: MOD_RES
<222> LOCATION: (11)..(11)
<223> OTHER INFORMATION: Ser(tBu)
<220> FEATURE:
<221> NAME/KEY: MOD_RES
<222> LOCATION: (12)..(12)
```

-continued

```
<223> OTHER INFORMATION: Ser(tBu)
<220> FEATURE:
<221> NAME/KEY: MOD_RES
<222> LOCATION: (13)..(13)
<223> OTHER INFORMATION: Tyr(tBu)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (17)..(17)
<223> OTHER INFORMATION: Gln(Trt)
<220> FEATURE:
<221> NAME/KEY: MOD_RES
<222> LOCATION: (20)..(20)
<223> OTHER INFORMATION: Lys(NH2)
<220> FEATURE:
<221> NAME/KEY: MOD_RES
<222> LOCATION: (21)..(21)
<223> OTHER INFORMATION: Glu(OtBu)
<220> FEATURE:
<221> NAME/KEY: MOD_RES
<222> LOCATION: (25)..(25)
<223> OTHER INFORMATION: Trp(Boc)
<220> FEATURE:
<221> NAME/KEY: MOD_RES
<222> LOCATION: (28)..(28)
<223> OTHER INFORMATION: Arg(Pbf)
<220> FEATURE:
<221> NAME/KEY: MOD_RES
<222> LOCATION: (30)..(30)
<223> OTHER INFORMATION: Arg(Pbf)
<220> FEATURE:
<221> NAME/KEY: MOD_RES
<222> LOCATION: (31)..(31)
<223> OTHER INFORMATION: Gly-O-2-CTC

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Boc-His(Trt)
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: Glu(OtBu)
<220> FEATURE:
<221> NAME/KEY: MOD_RES
<222> LOCATION: (5)..(5)
<223> OTHER INFORMATION: Thr(tBu)
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
```

-continued

```
<222> LOCATION: (9)..(9)
<223> OTHER INFORMATION: Asp(OtBu)
<220> FEATURE:
<221> NAME/KEY: MOD_RES
<222> LOCATION: (11)..(11)
<223> OTHER INFORMATION: Ser(tBu)
<220> FEATURE:
<221> NAME/KEY: MOD_RES
<222> LOCATION: (12)..(12)
<223> OTHER INFORMATION: Ser(tBu)
<220> FEATURE:
<221> NAME/KEY: MOD_RES
<222> LOCATION: (13)..(13)
<223> OTHER INFORMATION: Tyr(tBu)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (17)..(17)
<223> OTHER INFORMATION: Gln(Trt)
<220> FEATURE:
<221> NAME/KEY: MOD_RES
<222> LOCATION: (20)..(20)
<223> OTHER INFORMATION: Lys(Glu-OtBu-Palmitoyl)
<220> FEATURE:
<221> NAME/KEY: MOD_RES
<222> LOCATION: (21)..(21)
<223> OTHER INFORMATION: Glu(OtBu)
<220> FEATURE:
<221> NAME/KEY: MOD_RES
<222> LOCATION: (25)..(25)
<223> OTHER INFORMATION: Trp(Boc)
<220> FEATURE:
<221> NAME/KEY: MOD_RES
<222> LOCATION: (28)..(28)
<223> OTHER INFORMATION: Arg(Pbf)
<220> FEATURE:
<221> NAME/KEY: MOD_RES
<222> LOCATION: (30)..(30)
<223> OTHER INFORMATION: Arg(Pbf)
<220> FEATURE:
<221> NAME/KEY: MOD_RES
<222> LOCATION: (31)..(31)
<223> OTHER INFORMATION: Gly-O-2-CTC

<400> SEQUENCE: 10

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Boc-His(Trt)
<220> FEATURE:
<221> NAME/KEY: MOD_RES
<222> LOCATION: (3)..(3)
<223> OTHER INFORMATION: Glu(Otbu)
<220> FEATURE:
<221> NAME/KEY: MOD_RES
<222> LOCATION: (5)..(5)
<223> OTHER INFORMATION: Thr(tBu)
<220> FEATURE:
<221> NAME/KEY: MOD_RES
<222> LOCATION: (7)..(7)
<223> OTHER INFORMATION: Thr(tBu)
<220> FEATURE:
```

```
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Asp(OtBu)
<220> FEATURE:
<221> NAME/KEY: MOD_RES
<222> LOCATION: (11)..(11)
<223> OTHER INFORMATION: Ser(tBu)
<220> FEATURE:
<221> NAME/KEY: MOD_RES
<222> LOCATION: (12)..(12)
<223> OTHER INFORMATION: Ser(tBu)
<220> FEATURE:
<221> NAME/KEY: MOD_RES
<222> LOCATION: (13)..(13)
<223> OTHER INFORMATION: Tyr(tBu)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (17)..(17)
<223> OTHER INFORMATION: Gln(Trt)
<220> FEATURE:
<221> NAME/KEY: MOD_RES
<222> LOCATION: (20)..(20)
<223> OTHER INFORMATION: Lys(PEG2-PEG2-Glu-OtBu-18-tBu-oxooctadecanoyl)
<220> FEATURE:
<221> NAME/KEY: MOD_RES
<222> LOCATION: (21)..(21)
<223> OTHER INFORMATION: Glu(OtBu)
<220> FEATURE:
<221> NAME/KEY: MOD_RES
<222> LOCATION: (25)..(25)
<223> OTHER INFORMATION: Trp(Boc)
<220> FEATURE:
<221> NAME/KEY: MOD_RES
<222> LOCATION: (28)..(28)
<223> OTHER INFORMATION: Arg(Pbf)
<220> FEATURE:
<221> NAME/KEY: MOD_RES
<222> LOCATION: (30)..(30)
<223> OTHER INFORMATION: Arg(Pbf)
<220> FEATURE:
<221> NAME/KEY: MOD_RES
<222> LOCATION: (31)..(31)
<223> OTHER INFORMATION: Gly-O-2-CTC

<400> SEQUENCE: 11

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
                20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Boc-His(Trt)
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: Glu(OtBu)
```

```
<220> FEATURE:
<221> NAME/KEY: MOD_RES
<222> LOCATION: (5)..(5)
<223> OTHER INFORMATION: Thr(tBu)
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Asp(OtBu)
<220> FEATURE:
<221> NAME/KEY: MOD_RES
<222> LOCATION: (11)..(11)
<223> OTHER INFORMATION: Ser(tBu)
<220> FEATURE:
<221> NAME/KEY: MOD_RES
<222> LOCATION: (12)..(12)
<223> OTHER INFORMATION: Ser(tBu)
<220> FEATURE:
<221> NAME/KEY: MOD_RES
<222> LOCATION: (13)..(13)
<223> OTHER INFORMATION: Tyr(tBu)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (17)..(17)
<223> OTHER INFORMATION: Gln(Trt)
<220> FEATURE:
<221> NAME/KEY: MOD_RES
<222> LOCATION: (20)..(20)
<223> OTHER INFORMATION: Lys(PEG2-PEG2-Glu-Otbu-18-tBu-oxooctadecanoyl)
<220> FEATURE:
<221> NAME/KEY: MOD_RES
<222> LOCATION: (21)..(21)
<223> OTHER INFORMATION: OtBu
<220> FEATURE:
<221> NAME/KEY: MOD_RES
<222> LOCATION: (25)..(25)
<223> OTHER INFORMATION: Trp(Boc)
<220> FEATURE:
<221> NAME/KEY: MOD_RES
<222> LOCATION: (28)..(28)
<223> OTHER INFORMATION: Arg(Pbf)
<220> FEATURE:
<221> NAME/KEY: MOD_RES
<222> LOCATION: (30)..(30)
<223> OTHER INFORMATION: Arg(Pbf)
<220> FEATURE:
<221> NAME/KEY: MOD_RES
<222> LOCATION: (31)..(31)
<223> OTHER INFORMATION: Gly-O-2-CTC

<400> SEQUENCE: 12

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

PROCESS OF PREPARATION OF GLUCAGON-LIKE PEPTIDE-1 (GLP-1) RECEPTOR AGONISTS AND THEIR ANALOGS

SEQUENCE LISTING

The instant application contains a Sequence Listing which is submitted via the USPTO patent electronic filing system in TXT format (ACSII text) and is hereby incorporated by reference in its entirety. Said TXT file, created on Dec. 15, 2025, is named 02801-K&K (00530147).ST25 and is 13,235 bytes in size.

FIELD OF THE INVENTION

The present invention relates to pharmaceuticals. Specifically, the present invention relates to processes for preparing glucagon-like peptide-1 (glp-1) receptor agonists, their analogs and pharmaceutically acceptable salts thereof. More specifically, the present invention relates to processes for preparing glucagon-like peptide-1 (glp-1) receptor agonist including liraglutide, D-liraglutide, semaglutide and D-semaglutide. The present invention specifically relates to processes for preparing glucagon-like peptide-1 (glp-1) receptor agonists and their analogs, wherein the liraglutide, D-liraglutide, semaglutide and D-semaglutide produced, are substantially pure. The present invention also relates to preparation of glucagon-like peptide-1 (glp-1) receptor agonists and their analogs by solid phase and solution phase methods.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Glucagon-like peptide-1 (GLP-1) is produced by the gut, and in a glucose-dependent manner stimulates insulin secretion while inhibiting glucagon secretion, reduces appetite and energy intake, and delays gastric emptying. This drug class has also been demonstrated to promote weight loss and reduce SBP, which could be of benefit to patients with type 2 diabetes, Glucagon-like peptide-1 receptor agonists (GLP-1 RAs) came to market in the year 2005, as a new therapeutic classification, for clinical use in the management of type 2 diabetes mellitus (T2DM). Since 2005, there have been six approved products on the market, with the newest product being Semaglutide. The GLP-1R agonist Semaglutide has recently been registered to treat type 2 diabetes. Semaglutide has two amino acid substitutions compared to human GLP-1 (Aib(8), Arg(34)) and is derivatized at lysine 26.

Liraglutide, represented by Formula (I) is an analog of human GLP-1 and acts as a GLP-1 receptor agonist. It is indicated for the treatment of patients with type 2 diabetes to improve glycemic control. The peptide precursor of liraglutide is generally produced by a process that includes expression of recombinant DNA in *Saccharomyces cerevisiae*, and has been engineered to be 97% homologous to native human GLP-1 by substituting arginine for lysine at position 34.

Different processes for the preparation of liraglutide and Semaglutide have been reported. U.S. Pat. No. 7,572,884 discloses a process for preparing liraglutide by recombinant technology followed by acylation and removal of N-terminal extension. WO2017162650 discloses another process for the preparation of liraglutide comprising precipitation of the liraglutide peptide or of a precursor peptide by means of mixing it with an anti-solvent comprising di-isopropyl ether and acetonitrile. WO2014199397 discloses process for obtaining liraglutide by means of solid phase synthesis using Wang resin. Such processes suffer from one or more of the limitations like either being very specific, complex to be implemented at an industrial level, unsatisfactory purity profile and yield of the end product, or commercial non-viability.

Although there are synthetic processes known for the preparations of GLP1 receptor agonists, there is still need to explore novel synthetic schemes that are scalable, and economically viable. More particularly there still exists an unmet need for synthetic schemes that can overcome one or more deficiencies associated with the known arts such that the synthetic schemes of the present invention being adaptable as generic schemes suitable for preparing different glucagon-like peptide-1 (glp-1) receptor agonists and analogues thereof including liraglutide, D-liraglutide, semaglutide and D-semaglutide, especially with improved purity profile and applicable at an industrial scale.

OBJECTS OF THE INVENTION

An object of the present disclosure is to provide processes for preparing glucagon-like peptide-1 (glp-1) receptor agonists and their analogs, their pharmaceutically acceptable salts and formulations thereof that can satisfy the existing need and can overcome ore or more deficiencies found in the existing in the art.

An object of the present disclosure is to provide processes for preparing glucagon-like peptide-1 (glp-1) receptor agonists and analogs thereof that can be adapted as economically viable schemes.

An object of the present disclosure is to provide processes for preparing glucagon-like peptide-1 (glp-1) receptor agonists and analogs and thereof that can be adapted as industrially scalable schemes.

An object of the present disclosure is to provide processes for preparing glucagon-like peptide-1 (glp-1) receptor agonists and analogs that are substantially pure.

Another object of the present disclosure is to provide a chemical synthetic process for preparing liraglutide, D-liraglutide, semaglutide and D-semaglutide.

SUMMARY OF THE INVENTION

The present disclosure relates processes for preparing glucagon-like peptide-1 (glp-1) receptor agonists, their analogs and pharmaceutically acceptable salts thereof.

In one aspect, the present disclosure relates to the preparation of substantially pure (glp-1) receptor agonists or analogs thereof selected from liraglutide, D-liraglutide, semaglutide and D-semaglutide.

In another aspect, the present disclosure relates to the preparation of (glp-1) receptor agonists or analogs thereof selected from liraglutide, D-liraglutide, semaglutide and D-semaglutide by solid phase methods.

In another aspect, the present disclosure relates to the preparation of (glp-1) receptor agonists or analogs thereof selected from liraglutide, D-liraglutide, semaglutide and D-semaglutide by solution phase methods.

In yet another aspect, the present disclosure relates to a process for the preparation of (glp-1) receptor agonists or analogs thereof selected from liraglutide, D-liraglutide, semaglutide and D-semaglutide by solid phase or solution phase methods, employing FMOC strategy.

In yet another aspect, the present disclosure relates to a process for the preparation of (glp-1) receptor agonists or analogs thereof selected from liraglutide, D-liraglutide, semaglutide and D-semaglutide synthesized by repeating dipeptide fragments Fmoc-Arg(Pbf)-Gly-OH and Fmoc-Glu (OtBu)-Gly-OH.

In an aspect the present disclosure provides a process for the preparation of (glp-1) receptor agonists or analogs thereof comprising:

a) anchoring a dipeptide fragment Fmoc-Arg(Pbf)-Gly-OH to a resin, capping it, and;

b) subjecting the anchored fragment to multiple cycles of sequential coupling;
wherein,
multiple cycles comprise:
selectively deprotecting an amino group and coupling a C-terminus of one more dipeptide fragment Fmoc-Arg(Pbf)-Gly-OH to the anchored and deprotected fragment at N-terminus in the presence of a coupling agent,
selectively deprotecting an amino group and coupling the resultant fragment to a C-terminus of a next N-protected amino acid in the presence of a coupling agent,
repeating said coupling steps to obtain an amino acid sequence of a desired linear glucagon-like peptide-1 (glp-1) receptor agonist or analog thereof comprising the amino acid sequence of a desired linear glucagon-like peptide-1 (glp-1) receptor agonist analog;

c) removing a lysine side chain protecting group, followed by coupling with Fmoc-Glu-OtBu, followed by Fmoc deprotection and coupling of N-terminal of the peptide attached to the resin with a long chain fatty acid, and cleaving the peptide from the resin to obtain a linear crude desired glucagon-like peptide-1 (glp-1) receptor agonist; and d) optionally purifying the crude glucagon-like peptide-1 (glp-1) receptor agonist.

In still another aspect, the present disclosure relates to a process for the preparation of liraglutide comprising steps of:

a) anchoring a dipeptide fragment Fmoc-Arg(Pbf)-Gly-OH to a resin and capping it;

b) selectively deprotecting an amino group of the anchored dipeptide fragment;

c) coupling a carboxyl terminus of one more dipeptide fragment Fmoc-Arg(Pbf)-Gly-OH to the fragment of step (b) at N-terminus in the presence of a coupling agent;

d) selectively deprotecting an amino group of the fragment of step (c);

e) coupling a carboxyl terminus of a next N-protected amino acid to the fragment of step (d) in the presence of a coupling agent;

f) repeating steps d) and e) to form a peptide with respective amino acid sequence of liraglutide;

g) removing a lysine side chain protecting group, followed by coupling the peptide fragment of step (f) with Fmoc-Glu-OtBu followed by Fmoc deprotection and coupling of N-terminal of the peptide attached to the resin with palmitic acid;

h) cleaving the peptide from the resin to obtain linear crude liraglutide;

i) optionally purifying the crude liraglutide.

In still another aspect, the present disclosure relates to a process for the preparation of liraglutide comprising the steps of:

a) anchoring a dipeptide fragment Fmoc-Arg(Pbf)-Gly-OH to a resin and capping it;

b) selectively deprotecting an amino group of the fragment of step (a);

c) sequential coupling of dipeptide fragment Fmoc-Arg (Pbf)-Gly-OH to amino acid fragments Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Dde)-OH, Fmoc-Ala-OH, Fmoc-Ala-OH, Fmoc-Gln(Trt)-OH; dipeptide fragment Fmoc-Glu (OtBu)-Gly-OH to amino acid fragments Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr (tBu)-OH; dipeptide fragment Fmoc-Glu(OtBu)-Gly-OH to amino acid fragments Fmoc-Ala-OH and Boc-His(Trt)-OH in the presence of a coupling agent to obtain amino acid sequence of a linear crude liraglutide;

d) removing a lysine side chain protecting group, followed by coupling the peptide fragment of step (c) with Fmoc-Glu-OtBu followed by Fmoc deprotection and coupling of N-terminal of the peptide attached to the resin with palmitic acid;

e) cleaving the peptide from the resin to obtain linear crude liraglutide; and f) optionally purifying the crude liraglutide.

In one more aspect, the present disclosure provides a process for the preparation of D-liraglutide comprising the steps of:

a) anchoring a dipeptide fragment Fmoc-Arg(Pbf)-Gly-OH to a resin and capping it;

b) selectively deprotecting an amino group of the anchored dipeptide fragment;

c) coupling a carboxyl terminus of one more dipeptide fragment Fmoc-Arg(Pbf)-Gly-OH to the fragment of step (b) in the presence of a coupling agent;

d) selectively deprotecting an amino group of the fragment of step (c);

e) coupling a carboxyl terminus of a next N-protected amino acid to the fragment of step (d) in the presence of a coupling agent;

f) repeating steps d) and e) to form a peptide with respective amino acids sequence of D-liraglutide;

g) removing of a lysine side chain protecting group, followed by coupling with Fmoc-Glu-OtBu, followed by Fmoc deprotection and coupling of N-terminal of the peptide attached to the resin with palmitic acid;

h) cleaving the peptide from the resin to obtain linear crude D-liraglutide; and i) optionally purifying the crude D-liraglutide.

In still another aspect, the present disclosure relates to a process for the preparation of D-liraglutide comprising the steps of:

a) Anchoring a dipeptide fragment Fmoc-Arg(Pbf)-Gly-OH to a resin and capping it;

b) selectively deprotecting an amino group of the anchored fragment;

c) sequential coupling of dipeptide fragment Fmoc-Arg (Pbf)-Gly-OH to amino acid fragments Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Dde)-OH, Fmoc-Ala-OH, Fmoc-Ala-OH, Fmoc-Gln(Trt)-OH, dipeptide fragment Fmoc-Glu (OtBu)-Gly-OH to amino acid fragments Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr (tBu)-OH, dipeptide fragment Fmoc-Glu(OtBu)-Gly-OH to amino acid fragments Fmoc-D-Ala-OH and Boc-His(Trt)-OH in the presence of a coupling agent to obtain amino acid sequence of linear crude D-liraglutide;

d) removing of a lysine side chain protecting group, followed by coupling with Fmoc-Glu-OtBu, followed by Fmoc deprotection and coupling of N-terminal of the peptide attached to the resin with palmitic acid;

e) cleaving the peptide from the resin to obtain linear crude D-liraglutide; and f) optionally purifying the crude D-liraglutide.

In one aspect, the present disclosure provides a process for preparation of semaglutide comprising the steps of:

a) anchoring a dipeptide fragment Fmoc-Arg(Pbf)-Gly-OH to a resin and capping it;

b) selectively deprotecting an amino group of the anchored fragment;

c) coupling a carboxyl terminus of one more dipeptide fragment Fmoc-Arg(Pbf)-Gly-OH to the fragment of step (b) in the presence of a coupling agent;

d) selectively deprotecting an amino group of the fragment of step (c);

e) coupling a carboxyl terminus of a next N-protected amino acid to the fragment of step (d) in the presence of a coupling agent;

f) repeating steps d) and e) to form a peptide with respective amino acid sequence of semaglutide;

g) removing a lysine side chain protecting group, followed by coupling with Fmoc-PEG2-CH$_2$—COOH sequences, Fmoc-Glu-OtBu followed by Fmoc deprotection and coupling with oxaoctadecanoic acid;

h) cleaving the peptide from the resin to obtain linear crude semaglutide; and i) optionally purifying the crude semaglutide.

In one aspect, the present disclosure provides a process for preparation of semaglutide comprising the steps of:

a) anchoring a dipeptide fragment Fmoc-Arg(Pbf)-Gly-OH to a resin and capping it;

b) selectively deprotecting an amino group of the anchored fragment;

c) sequential coupling of dipeptide fragment Fmoc-Arg(Pbf)-Gly-OH to amino acid fragments Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Dde)-OH, Fmoc-Ala-OH, Fmoc-Ala-OH, Fmoc-Gln(Trt)-OH, dipeptide fragment Fmoc-Glu (OtBu)-Gly-OH, to amino acid fragments Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr (tBu)-OH, dipeptide fragment Fmoc-Glu(OtBu)-Gly-OH to amino acid fragments Fmoc-D-Ala-OH and Boc-His(Trt)-OH in the presence of a coupling agent to obtain a linear crude peptide with amino acid sequences of semaglutide;

d) removing a lysine side chain protecting group, followed by coupling with Fmoc-PEG2-CH$_2$—COOH sequences, Fmoc-Glu-OtBu followed by Fmoc deprotection and coupling with oxaoctadecanoic acid;

e) cleaving the peptide from the resin to obtain linear crude semaglutide; and f) optionally purifying the crude semaglutide.

In one aspect, the present disclosure provides a process for preparation of D-semaglutide comprising the steps of:

a) anchoring a dipeptide fragment Fmoc-Arg(Pbf)-Gly-OH to a resin and capping it;

b) selectively deprotecting an amino group of the anchored fragment;

c) coupling the carboxyl terminus of one more dipeptide fragment Fmoc-Arg(Pbf)-Gly-OH to the fragment of step (b) in the presence of a coupling agent;

d) selectively deprotecting an amino group of the fragment of step (c);

e) coupling a carboxyl terminus of a next N-protected amino acid to the fragment of step (d) in the presence of a coupling agent;

f) repeating steps d) and e) to form a peptide with respective amino acid sequence of D-semaglutide;

g) removing a lysine side chain protecting group, followed by coupling with Fmoc-PEG2-CH$_2$—COOH sequences, Fmoc-Glu-OtBu followed by Fmoc deprotection and coupling with oxaoctadecanoic acid;

h) cleaving the peptide from the resin to obtain linear crude D-semaglutide; and i) optionally purifying the crude D-Semaglutide.

In one aspect, the present disclosure provides a process for preparation of D-semaglutide comprising the steps of:

a) anchoring a dipeptide fragment Fmoc-Arg(Pbf)-Gly-OH to a resin and capping it;

b) selectively deprotecting an amino group of the anchored fragment;

c) sequential coupling of dipeptide fragment Fmoc-Arg(Pbf)-Gly-OH to amino acid fragments Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Dde)-OH, Fmoc-Ala-OH, Fmoc-Ala-OH, Fmoc-Gln(Trt)-OH, dipeptide fragment Fmoc-Glu (OtBu)-Gly-OH to amino acid fragments Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr (tBu)-OH, dipeptide fragment Fmoc-Glu(OtBu)-Gly-OH to amino acid fragments Fmoc-D-Ala-OH and Boc-His(Trt)-OH to obtain amino acid sequence of a linear crude D-semaglutide;

d) removing the lysine side chain protecting group, followed by coupling with Fmoc-PEG2-CH$_2$—COOH sequences, Fmoc-Glu-OtBu followed by Fmoc deprotection and coupling with oxaoctadecanoic acid;

e) cleaving the peptide from the resin to obtain linear crude D-semaglutide; and f) optionally purifying the crude D-semaglutide.

In still another aspect, the present disclosure provides a process for the preparation of a dipeptide fragment Fmoc-Arg(Pbf)-Gly-OH, the process comprising steps of:

e) anchoring Fmoc-Arg(Pbf)-OH to a resin and capping it;

f) selectively deprotecting an amino group of the anchored fragment;

g) coupling Glycine alkyl ester to the fragment of step (b) in the presence of a coupling agent;

h) cleaving the dipeptide fragment obtained in step (c) from the resin;

i) optionally purifying the crude dipeptide fragment Fmoc-Arg(Pbf)-Gly-OH.

In still another aspect, the present disclosure relates to a process for the preparation of a dipeptide fragment Fmoc-Glu(OtBu)-Gly-OH comprising steps of:

a) anchoring Fmoc-Glu(OtBu)-OH to a resin and capping it;

b) selectively deprotecting an amino group of the anchored fragment;

c) coupling Glycine alkyl ester to the fragment of step (b) in the presence of a coupling agent;

d) cleaving the dipeptide fragment obtained in step (c) from the resin;

e) optionally purifying the crude dipeptide fragment Fmoc-Glu(OtBu)-Gly-OH.

Various objects, features, aspects and advantages of the inventive subject matter will become more apparent from the following detailed description of preferred embodiments

BRIEF DESCRIPTION OF DRAWINGS THE INVENTION

The following drawings form part of the present specification and are included to further illustrate aspects of the present disclosure. The disclosure may be better understood by reference to the drawings in combination with the detailed description of the specific embodiments presented herein.

FIG. 1 is a flow-chart depicting a protocol for the preparation of liraglutide comprising the steps as shown in scheme 1 as per one of the exemplary embodiments.

FIG. 2 is a flow-chart depicting a protocol for the preparation of liraglutide comprising the steps as shown in scheme 2 as per one of the exemplary embodiments.

FIG. 3 is a flow-chart depicting a protocol for the preparation of D-liraglutide comprising the steps as shown in scheme 3 as per one of the exemplary embodiments.

FIG. 4 is a flow-chart depicting a protocol for the preparation of D-liraglutide comprising the steps as shown in scheme 4 as per one of the exemplary embodiments.

FIG. 5 is a flow-chart depicting a protocol for the preparation of semaglutide comprising the steps as shown in scheme 5 as per one of the exemplary embodiments.

FIG. 6 is a flow-chart depicting a protocol for the preparation of semaglutide comprising the steps as shown in scheme 6 as per one of the exemplary embodiments.

FIG. 8 is a flow-chart depicting a protocol for the preparation of D-semaglutide comprising the steps as shown in scheme 8 as per one of the exemplary embodiments.

DETAILED DESCRIPTION

Figure 7:
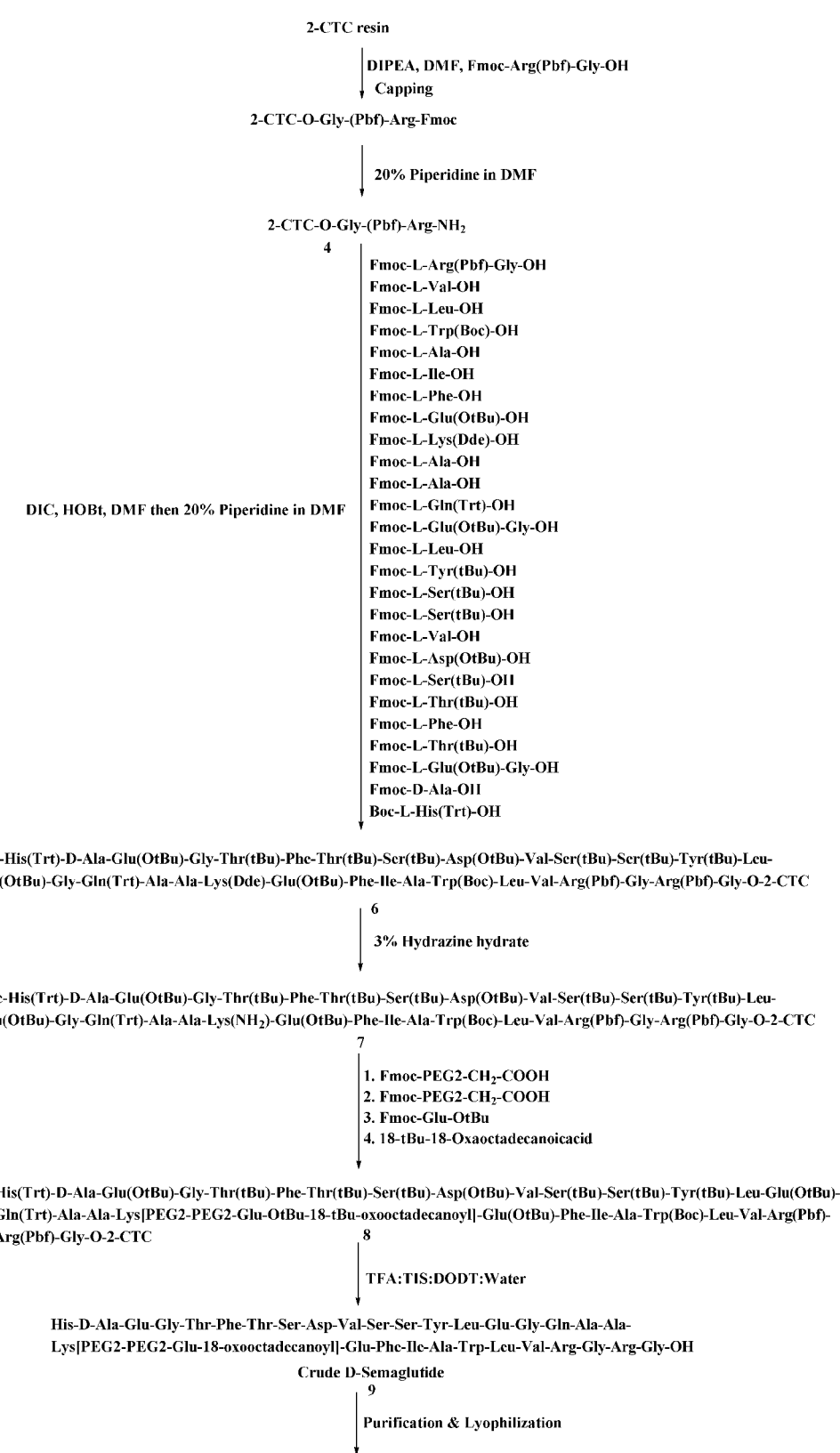
FIG. 7 is a flow-chart depicting a protocol for the preparation of D-semaglutide comprising the steps as shown in scheme 7 as per one of the exemplary embodiments.

The following is a detailed description of embodiments of the disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some embodiments, the numbers expressing quantities of ingredients, properties such as concentration, reaction conditions, and so forth, used to describe and claim certain embodiments of the disclosure are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable. The numerical values presented in some embodiments of the disclosure may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context requires otherwise, throughout the specification which follow, the word "comprise" and variations thereof, such as, "comprises" and "comprising" are to be construed in an open, inclusive sense that is as "including, but not limited to."

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The description that follows, and the embodiments described therein, is provided by way of illustration of an example, or examples, of particular embodiments of the principles and aspects of the present disclosure. These examples are provided for the purposes of explanation, and not of limitation, of those principles and of the disclosure.

It should also be appreciated that the present disclosure can be implemented in numerous ways, including as a system, a method or a device. In this specification, these implementations, or any other form that the invention may take, may be referred to as processes. In general, the order of the steps of the disclosed processes may be altered within the scope of the invention.

The headings and abstract of the invention provided herein are for convenience only and do not interpret the scope or meaning of the embodiments.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

Various terms as used herein are shown below. To the extent a term used in a claim is not defined below, it should be given the broadest definition persons in the pertinent art have given that term as reflected in printed publications and issued patents at the time of filing.

The present disclosure relates to processes for preparing glucagon-like peptide-1 (glp-1) receptor agonists, their analogs and pharmaceutically and acceptable salts thereof.

In one embodiment the present disclosure relates to a process for preparation of glucagon-like peptide-1 (glp-1) receptor agonist selected from liraglutide, D-liraglutide, semaglutide and D-semaglutide in substantially pure form.

Liraglutide, represented by Formula (I) is an analog of human GLP-1 and acts as a GLP-1 receptor agonist. It is indicated for the treatment of patients with type 2 diabetes to improve glycemic control. The peptide precursor of liraglutide is generally produced by a process that includes expression of recombinant DNA in *Saccharomyces cerevisiae*, and has been engineered to be 97% homologous to native human GLP-1 by substituting arginine for lysine at position 34. Liraglutide is made by attaching a C-16 fatty acid (palmitic acid) with a glutamic acid spacer on the remaining lysine residue at position 26 of the peptide precursor.

```
                                    Formula (I)
H-His-Ala-Glu-Gly-Thr-Phe-Thr-Ser-Asp-Val-Ser-Ser- Tyr-Leu-Glu-Gly-Gln-Ala-Ala-Lys (γ-Glu-palmitoyl)-

Glu-Phe-Ile-Ala-Trp-Leu-Val-Arg-Gly-

Arg-Gly-OH (SEQ ID NO: 1).
```

D-Liraglutide, is an analog of liraglutide represented by Formula (II) and acts as a GLP-1 receptor agonist. It is prepared by replacing the amino acid at position 2 of the native Liraglutide with D-Alanine.

```
                                    Formula (II)
H-His-D-Ala-Glu-Gly-Thr-Phe-Thr-Ser-Asp-Val-Ser- Ser-Tyr-Leu-Glu-Gly-Gln-Ala-Ala-Lys (γ-Glupalmitoyl)-Glu-Phe-Ile-Ala-Trp-Leu-Val-Arg-Gly-Arg- Gly-OH (SEQ ID NO: 2).
```

Semaglutide, represented by formula (III), is an analog of human GLP-1 and acts as a GLP-1 receptor agonist. The sequence of semaglutide has the main chain containing a 31 amino acid. A PEG, glutamic acid, and octadecanoic acid aliphatic chain are to be grafted to Lys at position 26 and an unnatural amino acid aminoisobutyric acid is located at position 8 thereof. The amino acid sequence of Semaglutide is:

```
                                    Formula (III)
H-His-Aib-Glu-Gly-Thr-Phe-Thr-Ser-Asp-Val-Ser-Ser- Tyr-Leu-Glu-Gly-Gln-Ala-Ala-Lys (PEG2-PEG2-Glu- 18oxooctadecanoyl)-Glu-Phe-Ile-Ala-Trp-Leu-Val- Arg-Gly-Arg-Gly-OH (SEQ ID NO: 3).
```

D-Semaglutide, represented by Formula (IV) is an analog of semaglutide and acts as a GLP-1 receptor agonist. This is prepared by replacing the amino acid at position 2 of the native Semaglutide with D-Alanine.

```
                                    Formula (IV)
H-His-D-Ala-Glu-Gly-Thr-Phe-Thr-Ser-Asp-Val-Ser- Ser-Tyr-Leu-Glu-Gly-Gln-Ala-Ala-Lys(PEG2-PEG2-Glu- 18oxooctadecanoyl)-Glu-Phe-Ile-Ala-Trp-Leu-Val- Arg-Gly-Arg-Gly-OH (SEQ ID NO: 4).
```

In an embodiment the present disclosure relates to a process for preparation of glucagon-like peptide-1 (glp-1) receptor agonist selected from liraglutide, D-liraglutide, semaglutide and D-semaglutide by solid phase or solution phase method.

In an embodiment, the present disclosure relates to a process for the preparation of glucagon-like peptide-1 (glp-1) receptor agonist selected from liraglutide, D-liraglutide, semaglutide and D-semaglutide by solid phase or solution phase method employing Fmoc strategy.

In yet another embodiment the present disclosure relates to a process for the preparation of (glp-1) receptor agonists or analogs thereof selected from liraglutide, D-liraglutide, semaglutide and D-semaglutide synthesized by repeating dipeptide fragments Fmoc-Arg(Pbf)-Gly-OH and Fmoc-Glu (OtBu)-Gly-OH.

In an embodiment the present disclosure provides a process for the preparation of (glp-1) receptor agonists or analogs thereof comprising steps of:
  a) anchoring a dipeptide fragment Fmoc-Arg(Pbf)-Gly-OH to a resin, capping it, and;
  b) subjecting the anchored fragment to multiple cycles of sequential coupling;

wherein, multiple cycles comprise:

selectively deprotecting an amino group and coupling a C-terminus of one more dipeptide fragment Fmoc-Arg(Pbf)-Gly-OH to the anchored and deprotected fragment at N-terminus in the presence of a coupling agent, selectively deprotecting an amino group and coupling the resultant fragment to a C-terminus of a next N-protected amino acid in the presence of a coupling agent repeating said coupling steps to obtain an amino acid sequence of a desired linear glucagon-like peptide-1 (glp-1) receptor agonist or analog thereof comprising the amino acid sequence of a desired linear glucagon-like peptide-1 (glp-1) receptor agonist analog;

c) removing a lysine side chain protecting group, followed by coupling with Fmoc-Glu-OtBu followed by Fmoc deprotection and coupling of N-terminal of the peptide attached to the resin with a long chain fatty acid; and cleaving the peptide from the resin to obtain a linear crude desired glucagon-like peptide-1 (glp-1) receptor agonist; and d) optionally purifying the crude glucagon-like peptide-1 (glp-1) receptor agonist.

In still another embodiment the present disclosure relates to a process for the preparation of liraglutide comprising steps of:

a) anchoring a dipeptide fragment Fmoc-Arg(Pbf)-Gly-OH to a resin and capping it;

b) selectively deprotecting an amino group of the anchored dipeptide fragment;

c) coupling a carboxyl terminus of one more dipeptide fragment Fmoc-Arg(Pbf)-Gly-OH to the fragment of step (b) at N-terminus in the presence of a coupling agent;

d) selectively deprotecting an amino group of the fragment of step (c);

e) coupling a carboxyl terminus of a next N-protected amino acid to the fragment of step (d) in the presence of a coupling agent;

f) repeating steps d) and e) to form a peptide with respective amino acid sequence of liraglutide;

g) removing a lysine side chain protecting group, followed by coupling the peptide fragment of step (f) with Fmoc-Glu-OtBu followed by Fmoc deprotection and coupling of N-terminal of the peptide attached to the resin with palmitic acid;

h) cleaving the peptide from the resin to obtain linear crude liraglutide;

i) optionally purifying the crude liraglutide.

In still another aspect, the present disclosure relates to a process for the preparation of liraglutide comprising the steps of:

g) anchoring a dipeptide fragment Fmoc-Arg(Pbf)-Gly-OH to a resin and capping it;

h) selectively deprotecting an amino group of the fragment of step (a);

i) sequential coupling of the dipeptide fragment Fmoc-Arg(Pbf)-Gly-OH, to amino acid fragments Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Dde)-OH, Fmoc-Ala-OH, Fmoc-Ala-OH, Fmoc-Gln(Trt)-OH; dipeptide fragment Fmoc-Glu(OtBu)-Gly-OH, to amino acid fragments Fmoc-Leu-OH, Fmoc-Tyr(tBu)-OH, Fmoc-Ser(tBu)-OH, Fmoc- Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr(tBu)-OH; dipeptide fragment Fmoc-Glu(OtBu)-Gly-OH, to amino acid fragments Fmoc-Ala-OH and Boc-His(Trt)-OH in the presence of a coupling agent to obtain a linear crude liraglutide;

j) removing a lysine side chain protecting group, followed by coupling the peptide fragment of step (c) with Fmoc-Glu-OtBu followed by Fmoc deprotection and coupling of N-terminal of the peptide attached to the resin with palmitic acid;

k) cleaving the peptide from the resin to obtain linear crude liraglutide; and l) optionally purifying the crude liraglutide.

In one more embodiment, the present disclosure provides a process for the preparation of D-liraglutide comprising the steps of:

a) anchoring a dipeptide fragment Fmoc-Arg(Pbf)-Gly-OH to a resin and capping it;

b) selectively deprotecting an amino group of the anchored dipeptide fragment;

c) coupling a carboxyl terminus of one more dipeptide fragment Fmoc-Arg(Pbf)-Gly-OH to the fragment of step (b) in the presence of a coupling agent;

d) selectively deprotecting an amino group of the fragment of step (c);

e) coupling a carboxyl terminus of a next N-protected amino acid to the fragment of step (d) in the presence of a coupling agent;

f) repeating steps d) and e) to form a peptide with respective amino acid sequence of D-liraglutide;

g) removing of a lysine side chain protecting group, followed by coupling with Fmoc-Glu-OtBu, followed by Fmoc deprotection and coupling of N-terminal peptide attached to resin with palmitic acid;

h) cleaving the peptide from the resin to obtain linear crude D-liraglutide; and i) optionally purifying the crude D-liraglutide.

In still another embodiment the present disclosure relates to a process for the preparation of D-liraglutide comprising the steps of:

a) anchoring a dipeptide fragment Fmoc-Arg(Pbf)-Gly-OH to a resin and capping it;

b) selectively deprotecting an amino group of the anchored fragment;

c) sequential coupling of the dipeptide fragment Fmoc-Arg(Pbf)-Gly-OH, to amino acid fragments Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Dde)-OH, Fmoc-Ala-OH, Fmoc-Ala-OH, Fmoc-Gln(Trt)-OH; dipeptide fragment Fmoc-Glu(OtBu)-Gly-OH, to amino acid fragments Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr(tBu)-OH; dipeptide fragment Fmoc-Glu(OtBu)-Gly-OH, to amino acid fragments Fmoc-D-Ala-OH and Boc-His(Trt)-OH in the presence of a coupling agent to obtain amino acid sequence of linear crude D-liraglutide;

d) removing of a lysine side chain protecting group, followed by coupling with Fmoc-Glu-OtBu, followed by Fmoc deprotection and coupling of N-terminal of the peptide attached to the resin with palmitic acid;

e) cleaving the peptide from the resin to obtain linear crude D-liraglutide; and f) optionally purifying the crude D-liraglutide.

In one embodiment, the present disclosure provides a process for preparation of semaglutide comprising the steps of:

a) anchoring a dipeptide fragment Fmoc-Arg(Pbf)-Gly-OH to a resin and capping it;

b) selectively deprotecting an amino group of the anchored fragment;

c) coupling a carboxyl terminus of one more dipeptide fragment Fmoc-Arg(Pbf)-Gly-OH to the fragment of step (b) in the presence of a coupling agent;

d) selectively deprotecting an amino group of the fragment of step (c);

e) coupling a carboxyl terminus of a next N-protected amino acid to the fragment of step (d) in the presence of a coupling agent;

f) repeating steps d) and e) to form a peptide with respective amino acid sequence of semaglutide sequence;

g) removing a lysine side chain protecting group, followed by coupling with Fmoc-PEG2-CH₂—COOH sequences, Fmoc-Glu-OtBu followed by Fmoc deprotection and coupling with oxaoctadecanoic acid;

h) cleaving the peptide from the resin to obtain linear crude semaglutide; and i) optionally purifying the crude semaglutide.

In one embodiment, the present disclosure provides a process for preparation of semaglutide comprising the steps of:

a) anchoring a dipeptide fragment Fmoc-Arg(Pbf)-Gly-OH to a resin and capping it;

b) selectively deprotecting an amino group of the anchored fragment;

c) sequential coupling of the dipeptide fragment Fmoc-Arg(Pbf)-Gly-OH, to amino acid fragments Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Dde)-OH, Fmoc-Ala-OH, Fmoc-Ala-OH, Fmoc-Gln(Trt)-OH; dipeptide fragment Fmoc-Glu(OtBu)-Gly-OH, to amino acid fragments Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr(tBu)-OH; dipeptide fragment Fmoc-Glu(OtBu)-Gly-OH, to amino acid fragments Fmoc-D-Ala-OH and Boc-His(Trt)-OH in the presence of a coupling agent to obtain a linear crude peptide with amino acid sequences of semaglutide;

d) removing a lysine side chain protecting group, followed by coupling with Fmoc-PEG2-CH₂—COOH sequences, Fmoc-Glu-OtBu followed by Fmoc deprotection and coupling with oxaoctadecanoic acid;

e) cleaving the peptide from the resin to obtain linear crude semaglutide; and f) optionally purifying the crude semaglutide.

In one embodiment, the present disclosure provides a process for preparation of D-semaglutide comprising the steps of:

a) anchoring a dipeptide fragment Fmoc-Arg(Pbf)-Gly-OH to a resin and capping it;

b) selectively deprotecting an amino group of the anchored fragment;

c) coupling the carboxyl terminus of one more dipeptide fragment Fmoc-Arg(Pbf)-Gly-OH to the fragment of step (b) in the presence of a coupling agent;

d) selectively deprotecting an amino group of the fragment of step (c);

e) coupling a carboxyl terminus of a next N-protected amino acid to the fragment of step (d) in the presence of a coupling agent;

f) repeating steps d) and e) to form a peptide with respective amino acid sequence of D-semaglutide;

g) removing a lysine side chain protecting group, followed by coupling with Fmoc-PEG2-CH₂—COOH sequences, Fmoc-Glu-OtBu followed by Fmoc deprotection and coupling with oxaoctadecanoic acid;

h) cleaving the peptide from the resin to obtain linear crude D-semaglutide; and i) optionally purifying the crude D-Semaglutide.

In one embodiment, the present disclosure provides a process for preparation of D-semaglutide comprising the steps of:

a) anchoring a dipeptide fragment Fmoc-Arg(Pbf)-Gly-OH to a resin and capping it;

b) selectively deprotecting an amino group of the anchored fragment;

c) sequential coupling of the fragments dipeptide fragment Fmoc-Arg(Pbf)-Gly-OH, to amino acid fragments Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Dde)-OH, Fmoc-Ala-OH, Fmoc-Ala-OH, Fmoc-Gln(Trt)-OH; dipeptide fragment Fmoc-Glu(OtBu)-Gly-OH, to amino acid fragments Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr(tBu)-OH; dipeptide fragment Fmoc-Glu(OtBu)-Gly-OH, to amino acid fragments Fmoc-D-Ala-OH and Boc-His(Trt)-OH to obtain amino acid sequence of a linear crude D-semaglutide; d) removing the lysine side chain protecting group, followed by coupling with Fmoc-PEG2-CH₂—COOH sequences, Fmoc-Glu-OtBu followed by Fmoc deprotection and coupling with oxaoctadecanoic acid;

e) cleaving the peptide from the resin to obtain linear crude D-semaglutide; and f) optionally purifying the crude D-semaglutide.

In still another embodiment, the present disclosure provides a process for the preparation of a dipeptide fragment Fmoc-Arg(Pbf)-Gly-OH, the process comprising steps of:

a) anchoring Fmoc-Arg(Pbf)-OH to a resin and capping it;

b) selectively deprotecting an amino group of the anchored fragment;

c) coupling Glycine alkyl ester to the fragment of step (b) in the presence of a coupling agent;

d) cleaving the dipeptide fragment obtained in step (c) from the resin;

e) optionally purifying the crude dipeptide fragment Fmoc-Arg(Pbf)-Gly-OH.

In still another embodiment, the present disclosure relates to a process for the preparation of a dipeptide fragment Fmoc-Glu(OtBu)-Gly-OH comprising steps of:

a) anchoring Fmoc-Glu(OtBu)-OH to a resin and capping it;

b) selectively deprotecting an amino group of the anchored fragment;

c) coupling Glycine alkyl ester to the fragment of step (b) in the presence of a coupling agent;

d) cleaving the dipeptide fragment obtained in step (c) from the resin;

e) optionally purifying the crude dipeptide fragment Fmoc-Glu(OtBu)-Gly-OH.

In an embodiment the deprotection of amino group is carried out of arginine.

In one embodiment the solid phase is a resin.

In one embodiment the resin is selected from but not limited to 2-Chlorotrityl chloride (2-CTC), Sasrin, entaGel S, TentaGel TGA, Rink, Wang, AmphiSpheres and other suitable resins.

In one embodiment capping is carried out with capping agent selected from but not limited to N,N-Diisopropyleth-ylamine (DIPEA), methanol, acetic anhydride and combi-nation thereof.

In one embodiment coupling agent is selected from but not limited to 1-Hydroxybenzotriazole (HOBt), N,N-diiso-propylcarbodiimide (DIC), Hexafluorophosphate Benzotri-azole Tetramethyl Uronium (HBTU), N,N-Diisopropyleth-ylamine (DIPEA), benzotriazol-1-yl-oxy-tris(dimethyl-amino)-phosphonium hexafluorophosphate (BOP), 0-(7-azabenzotriazol-1-yl)-1,1,3,3-tetramethyluronium hexafluorophosphate (HATU) and combination thereof.

In one embodiment the solvent for coupling reaction is selected from but not limited to DMF, pyridine, acetic anhydride, methanol, ethanol, isopropanol, dichloroethane, 1,4-dioxane, 2-methyl tetrahydrofuran, N-methyl-2-pyrroli-dinone (NMP), ethyl acetate, acetonitrile, acetone, and the like or combination thereof.

In one embodiment one or more repeating dipeptide fragments like Fmoc-Arg(Pbf)-Gly-OH and Fmoc-Glu (OtBu)-Gly-OH are synthesized by solution phase method.

In one embodiment the amino group can be selectively deprotected by methods known in the art for example by using a mixture of piperidine, DBU and dichloromethane in an appropriate solvent such as DMF.

In one embodiment peptide formed can be cleaved from the resin using chemicals selected from but not limited to difluoroacetic acid, trifluoro acetic acid and the like.

In an embodiment the purification process of GLP-1 analogs selected from liraglutide, D-liraglutide, Semaglutide or D-Semaglutide can be carried out by the processes well known in art. Purification process can be selected from but not limited to preparative reverse phase HPLC, ion exchange chromatography, size exclusion chromatography affinity chromatography and the like.

In one embodiment, the present disclosure provides a process for purifying glucagon-like peptide-1 (glp-1) recep-tor agonist or analog thereof of any of the preceding claims, the process comprising:

a) subjecting the crude GLP1 receptor agonist or analog thereof to a first HPLC purification with a mobile phase comprising ammonium bicarbonate and acetonitrile having pH 8.5-9.5;

b) collecting and combining pooled fractions from step (a) and subjecting to a second HPLC purification with an eluting mobile phase comprising trifluoro acetic acid and acetonitrile at a linear gradient from 30% B to 45% B;

c) subjecting the fraction obtained from the second HPLC purification in step (b) to a third HPLC purification with a mobile phase comprising ammonium hydroxide, acetonitrile, ammonium acetate, and purified water;

d) concentrating the fraction obtained from the third HPLC purification in step (c) and subjecting to lyo-philization to provide the purified glp-1 receptor ago-nist or analog thereof.

In one embodiment the use of two dipeptide fragments selected from Fmoc-Arg(Pbf)-Gly-OH and Fmoc-Glu (OtBu)-Gly-OH helps in reducing the respective Endo-Gly impurities.

In another embodiment, the present disclosure relates to the process for the preparation of liraglutide which com-prises the steps as shown in scheme 1.

In another embodiment, the present disclosure relates to the process for the preparation of liraglutide which com-prises the steps as shown in scheme 2.

In another embodiment, the present disclosure relates to the process for the preparation of D-liraglutide which com-prises the steps as shown in scheme 3.

In another embodiment, the present disclosure relates to the process for the preparation of D-liraglutide which com-prises the steps as shown in scheme 4.

In another embodiment, the present disclosure relates to the process for the preparation of semaglutide which com-prises the steps as shown in scheme 5.

In another embodiment, the present disclosure relates to the process for the preparation of semaglutide which com-prises the steps as shown in scheme 6.

In another embodiment, the present disclosure relates to the process for the preparation of D-semaglutide which comprises the steps as shown in scheme 7.

In another embodiment, the present disclosure relates to the process for the preparation of D-semaglutide which comprises the steps as shown in scheme 8.

In another embodiment, the present disclosure relates to the process for the preparation of glucagon-like peptide-1 (glp-1) receptor agonists or analogs thereof wherein the use of two dipeptide fragments Fmoc-Arg(Pbf)-Gly-OH and Fmoc-Glu(tBu)-Gly-OH helps in reducing the respective Endo-Gly impurities.

In another embodiment, the present disclosure also pro-vides a process for purifying glucagon-like peptide-1 (glp-1) receptor agonist or analog thereof, the process comprises:

a) subjecting the crude GLP1 receptor agonist or analog thereof to a first HPLC purification with a mobile phase comprising ammonium bicarbonate and acetonitrile having pH 8.5-9.5;

b) collecting and combining pooled fractions from step (a) and subjecting to a second HPLC purification with an eluting mobile phase comprising trifluoro acetic acid and acetonitrile at a linear gradient from 30% B to 45% B;

c) subjecting the fraction obtained from the second HPLC purification in step (b) to a third HPLC purification with a mobile phase comprising ammonium hydroxide, acetonitrile, ammonium acetate, and purified water;

d) concentrating the fraction obtained from the third HPLC purification in step (c) and subjecting to lyo-philization to provide the purified glp-1 receptor ago-nist or analog thereof.

The present disclosure provides processes for providing glucagon-like peptide-1 (glp-1) receptor agonist or analog thereof with substantial purity, such processes being scalable at an industrial level.

While the foregoing describes various embodiments of the disclosure, other and further embodiments of the disclo-sure may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

EXAMPLES

The present invention is further explained in the form of following examples. However, it is to be understood that the following examples are merely illustrative and are not to be taken as limitations upon the scope of the invention.

Abbreviations

Boc: t-Butyloxycarbonyl
DCM: Dichloromethane
DIC: N,N'-Diisopropylcarbodiimide
DIPEA: Diisopropylethylamine
DMF: Dimethylformamide
DODT: 2,2'-(Ethylenedioxy)diethanethiol
Fmoc: 9-Fluorenylmethoxycarbonyl
HBTU: Hexafluorophosphate benzotriazole tetramethyluronium
HOBt: N-Hydroxybenzotriazole
HPLC: High Performance Liquid Chromatography
MTBE: Methyl-t-butyl ether
OBt: O-Benzotriazole
OtBu: tert-Butyl ester
tBu: tert-Butyl
TFA: Trifluoroacetic acid
Trt: Trityl
2-CTC: 2-Chlorotrityl chloride
HCl: Hydrochloric acid
NaHCO$_3$: Sodium bicarbonate
Na$_2$SO$_4$: Sodium sulphate
TLC: Thin Layer Chromatography
LiOH: Lithium hydroxide
mL: millilitre
g: gram
° C.: degree Celsius
h: hour
min: minutes
IPA: Isopropanol
vol: Volumes
RT: Room Temperature
Mmol: Milli mole
w/v: weight/volume
TIPS: Triisopropylsilane
A°: Angstrom
HPLC: High Performance Liquid Chromatography

Example 1

Synthesis of Liraglutide
Step 1: Preparation of Fragment Fmoc-Arg(Pbf)-Gly-OH (1)

Fmoc—Arg(Pbf)—OH  +  HCl·Gly—OMe  or  HCl·Gly—OEt  →(HBTU, HOBt, DMF / 25-30° C., 2-3 h)

1a

1b

-continued

Fmoc—Arg(Pbf)—Gly—OMe  or  Fmoc—Arg(Pbf)—Gly—OEt  →(LiOH, Water:THF / 25-30° C., 2-3 h)

1c

Fmoc—Arg(Pbf)—Gly—OH

1

To the mixture of Fmoc-Arg(Pbf)-OH (1a) (20 mmol, 12.96 g), HBTU (30 mmol, 11.38 g) and HOBT (30 mmol, 4.6 g) dissolved in 100 mL DMF, DIPEA (40 mmol, 7.0 mL) was added. After the mixture was stirred for 5 min at room temperature, Glycine methylester hydrochloride or Glycine ethylester hydrochloride (1b) (40 mmol, 5.6 g) was added. The reaction was stirred for another 2-3 h. The progress of the reaction was monitored by TLC. Then the reaction was quenched by adding 60 mL water and extracted with ethyl acetate. The combined organic phase was washed with aqueous 0.5N HCl soln., aq. 5% NaHCO$_3$ soln. brine, dried over Na$_2$SO$_4$, concentrated and purified using flash column chromatography to give the Fmoc-Arg(Pbf)-Gly-OMe or Fmoc-Arg(Pbf)-Gly-OEt (1c) (12.5 g, 86%).

To the solution of Fmoc-Arg(Pbf)-Gly-OMe or Fmoc-Arg(Pbf)-Gly-OEt (1c) (12.5 g) in THF-water (4:1) (200 mL) at 0° C., the solution of LiOH.H$_2$O (1.58 g, 38 mmol) in 40 mL water was added in small portions over a period of 10 min. After stirring at 0° C. for another 40 min, the reaction mixture was adjusted to pH 3-4 by adding 2.5% (w/v) citric acid solution and extracted using ethyl acetate. The combined organic layer was washed with brine, dried over Na$_2$SO$_4$, concentrated, and purified using flash column chromatography to give fragment Fmoc-Arg(Pbf)-Gly-OH (1) as white solid (8.5 g, 71%).

Step 2: Preparation of Fragment Fmoc-Glu(OtBu)-Gly-OH (2)

Fmoc—Glu(OtBu)—OH  +  HCl·Gly—OMe  or  HCl·Gly—OEt  →(HBTU, HOBt, DMF / 25-30° C., 2-3 h)

2a

1b

Fmoc—Glu(OtBu)—Gly—OMe  or  Fmoc—Glu(OtBu)—Gly—OEt  →(LiOH, Water:THF / 25-30° C., 2-3 h)

2b

Fmoc—Glu(OtBu)—Gly—OH

2

To the mixture of Fmoc-Glu(OtBu)-OH (2a) (20 mmol, 8.5 g), HBTU (30 mmol, 11.38 g) and HOBt (30 mmol, 4.6 g) dissolved in 100 mL DMF, DIPEA (40 mmol, 7.0 mL) was added. After the mixture was stirred for 5 min at room temperature, HCl.Gly-OMe or HCl.Gly-OEt (1b) (40 mmol, 5.6 g) was added. The reaction was stirred for another 2-3 h. The progress of the reaction was monitored by TLC. Then the reaction was quenched by adding 60 mL water and extracted with ethyl acetate. The combined organic phase was washed with aq. 0.5N HCl soln., aq. 5% NaHCO$_3$ soln. brine, dried over Na$_2$SO$_4$, concentrated and purified using flash column chromatography to give the Fmoc-Glu(OtBu)-Gly-OMe or Fmoc-Glu(OtBu)-Gly-OEt (2b) (8.0 g, 89%).

To the solution of Fmoc-Glu(OtBu)-Gly-OMe or Fmoc-Glu(OtBu)-Gly-OEt (2b) (8.0 g) in THF-water (4:1) (200 mL) at 0° C., the solution of LiOH.H$_2$O (1.58 g, 38 mmol) in 40 mL water was added in small portions over a period of 10 min. After stirring at 0° C. for another 40 min, the reaction mixture was adjusted to pH 3-4 by adding 2.5% (w/v) citric acid solution and extracted using ethyl acetate. The combined organic layer was washed with brine, dried over Na$_2$SO$_4$, concentrated, and purified using flash column chromatography to give Fmoc-Glu(tBu)-Gly-OH (2) as white solid (5.6 g, 70%).

Step 3: Anchoring of Fragment (1) on Resin $$\text{2-CTC resin} \ + \ \text{Fmoc}\text{—}\text{Arg(Pbf)}\text{—}\text{Gly}\text{—}\text{OH} \xrightarrow[\substack{25\text{-}30°\ \text{C.,}\\2\text{-}3\ \text{h}}]{\text{DIPEA,}\\ \text{DMF}}$$

$$\underset{3}{\text{Fmoc}\text{—}\text{Arg(Pbf)}\text{—}\text{Gly}\text{—}\text{O-2-CTC}}$$

Resin (50 g, substitution=1.0 mmol/g resin) was charged into a peptide synthesis flask and washed twice with dichloromethane (500 mL, 10 vol). The resin was suspended in dichloromethane (DCM) (500 mL, 10 vol) without stirring for 30 min. The resin was added with a clear mixture of Fmoc-Arg(Pbf)-Gly-OH (1) (2.0 equiv), DIPEA (3.0 equiv) and DMF (500 mL, 10 vol). The suspension was gently agitated under nitrogen bubbling and mild stirring at 25-30° C. for 2.0 h. The reaction mass was then drained and resin washed with DMF (3×10 vol) and DCM (3×10 vol). The resin was added with a mixture of 10% DIPEA in methanol. The suspension was stirred for 30 min and drained. The resin washed with DMF (5×10 vol). this gives Fmoc resin fragment (3).

Step 4: Preparation of Deprotected Fragment (4)

$$\underset{3}{\text{Fmoc}\text{—}\text{Arg(Pbf)}\text{—}\text{Gly}\text{—}\text{O-2-CTC}} \xrightarrow{\substack{20\%\ \text{Piperidine}\\ \text{in DMF}}}$$

$$\underset{4}{\text{H}_2\text{N}\text{—}\text{Arg(Pbf)}\text{—}\text{Gly}\text{—}\text{O-2-CTC}}$$

The Fmoc resin fragment (3) was added with a clear mixture of 20% piperidine in DMF lot-1 (10 vol). The suspension was gently agitated under nitrogen bubbling and mild stirring at 25-30° C. for 10 min. The solvent was drained and the resin was added with a clear mixture of 20% piperidine in DMF lot-2 (10 vol). The suspension was stirred at 25-30° C. for 10 min. The solvent was drained and the resin was washed with DMF (2×10 vol) and IPA (1×10 vol) and DMF (2×10 vol). Completion of the Fmoc-deprotection to obtain deprotected Fragment (4) was confirmed by Kaiser colour test.

Step 5: Preparation of Fragment Fmoc-Arg(Pbf)-Gly-Arg(Pbf)-CTC (5)

$$\underset{4}{\text{H}_2\text{N}\text{—}\text{Arg(Pbf)}\text{—}\text{Gly}\text{—}\text{O-2-CTC}} \ + $$

$$\underset{1}{\text{Fmoc}\text{—}\text{Arg(Pbf)}\text{—}\text{Gly}\text{—}\text{OH}} \xrightarrow{\text{DIC, HOBt}}$$

-continued $$\underset{5}{\text{Fmoc}\text{—}\text{Arg(Pbf)}\text{—}\text{Gly}\text{—}\text{Arg(Pbf)}\text{—}\text{Gly}\text{—}\text{O-2-CTC}}$$

A clear mixture of Fmoc-Arg(Pbf)-Gly-OH (1) (2.0 equiv), N,N-diisopropylcarbodiimide (DIC) (2.0 equiv) and 1-Hydroxybenzotriazole (HOBt) (2.0 equiv) in DMF (10 vol) was coupled to the deprotected Fragment (4). The suspension was gently agitated under nitrogen bubbling and mild stirring at 25-30° C. for 2.0 h. Progress of the reaction was monitored by Kaiser colour test. After completion of the reaction, the reaction solvent was drained and resin washed with DMF (4×10 vol).

Step 6: Sequential Coupling of Other Fmoc-Protected Amino Acids (6)

A clear mixture of Fmoc-protected amino acid [Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Dde)-OH, Fmoc-Ala-OH, Fmoc-Ala-OH, Fmoc-Gln(Trt)-OH, Fmoc-Glu(OtBu)-Gly-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr(tBu)-OH, Fmoc-Glu(OtBu)-Gly-OH, Fmoc-Ala-OH and Boc-His(Trt)-OH] (2.0 equiv), N,N-diisopropylcarbodiimide (DIC) (2.0 equiv) and 1-Hydroxybenzotriazole (HOBt) (2.0 equiv) in DMF (10 vol) was added to the resin. The suspension was gently agitated under nitrogen bubbling and mild stirring at 45-55° C. for 20-45 min. Progress of the reaction was monitored by Kaiser colour test. After completion of the reaction, the reaction solvent was drained and resin washed with DMF (4×10 vol).

The same process as of Step-4 for Fmoc-deprotection was followed for all the above amino acid fragments deprotection.

Step 7: Preparation of N-[1-(4,4-dimethyl-2,6-dioxocyclohex-1-ylidene) ethyl](Dde) Deprotected Resin Fragment (7)

(SEQ ID NO: 5)

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Dde)-Glu(OtBu)-Phe-Ile-Ala-Trt(Boc)-Leu-Val-Arg(Pbf)-Gly-A$^6$rg(Pbf)-Gly-O-2-CTC $$\Big\downarrow \text{3\% Hydrazine hydrate}$$

(SEQ ID NO: 6)

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(NH$_2$)-Glu(OtBu)-Phe-Ile-Ala-Trt(Boc)-Leu-Val-Arg(Pbf)-Gly-Arg(Pbf)-Gly-O-2-CTC

7

The resin fragment (6) was added with a clear mixture of 3% Hydrazine hydrate in DMF lot-1 (10 vol). The suspension was gently agitated under nitrogen bubbling and mild stirring at 25-30° C. for 10 min. The solvent was drained and the resin was added with a clear mixture of 3% Hydrazine hydrate in DMF lot-2 (10 vol). The suspension was stirred at 25-30° C. for 10 min. The solvent was drained and the resin was washed with DMF (2×10 vol) and IPA (1×10 vol) and DMF (2×10 vol). Completion of the Dde-deprotection was confirmed by Kaiser colour test.

Step 8: Coupling of Fmoc-Glu-OtBu and Palmitic Acid (SEQ ID NO: 6)

Boc-His(Trt)-Ala-Glu(OtBu)-Gly-Thr(tBu)-Phe-Thr(tBu)-Ser(tBu)-
Asp(OtBu)-Val-Ser(tBu)-Ser(tBu)-Tyr(tBu)-Leu-Glu(OtBu)-Gly-
Gln(Trt)-Ala-Ala-Lys(NH₂)-Glu(OtBu)-Phe-Ile-Ala-Trp(Boc)-
Leu-Val-Arg(Pbf)-Gly-Arg(Pbf)-Gly-O-2-CTC

7

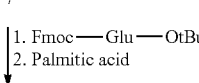

1. Fmoc—Glu—OtBu
2. Palmitic acid (SEQ ID NO: 7)

Boc-His(Trt)-Ala-Glu(OtBu)-Gly-Thr(tBu)-Phe-Thr(tBu)-Ser(tBu)-
Asp(OtBu)-Val-Ser(tBu)-Ser(tBu)-Tyr(tBu)-Leu-Glu(OtBu)-Gly-
Gln(Trt)-Ala-Ala-Lys(Glu-OtBu-Palmitoyl)-Glu(OtBu)-Phe-Ile-Ala-
Trp(Boc)-Leu-Val-Arg(Pbf)-Gly-Arg(Pbf)-Gly-O-2-CTC

8

Step (8a): Coupling of Fmoc-Glu-OtBu

A clear mixture of Fmoc-Glu-OtBu (2.0 equiv), N,N-diisopropylcarbodiimide (DIC) (2.0 equiv) and 1-Hydroxy-benzotriazole (HOBt) (2.0 equiv) in DMF (10 vol) was added to the resin. The suspension was gently agitated under nitrogen bubbling and mild stirring at 45-55° C. for 30 min. Progress of the reaction was monitored by Kaiser colour test. After completion of the reaction, the reaction solvent was drained and resin washed with DMF (4×10 vol).

Step (8b): Fmoc-Deprotection

The resin was added with a clear mixture of 20% piperidine in DMF lot-1 (10 vol). The suspension was gently agitated under nitrogen bubbling and mild stirring at 25-30° C. for 10 min. The solvent was drained and the resin was added with a clear mixture of 20% piperidine in DMF lot-2 (10 vol). The suspension was stirred at 25-30° C. for 10 min. The solvent was drained and the resin was washed with DMF (2×10 vol) and IPA (1×10 vol) and DMF (2×10 vol). Completion of the Fmoc-deprotection was confirmed by Kaiser colour test.

Step (8c): Coupling of Palmitic Acid

A clear mixture of Palmitic acid (2.0 equiv), N,N-diisopropylcarbodiimide (DIC)(2.0 equiv) and 1-Hydroxybenzotriazole (HOBt)(2.0 equiv) in DMF (10 vol) was added to the resin. The suspension was gently agitated under nitrogen bubbling and mild stirring at 45-55° C. for 30 min. Progress of the reaction was monitored by Kaiser colour test. After completion of the reaction, the reaction solvent was drained and resin washed with DMF (4×10 vol).

Step 9: Preparation of Crude Liraglutide (9)

(SEQ ID NO: 7)

Boc-His(Trt)-Ala-Glu(OtBu)-Gly-Thr(tBu)-Phe-Thr(tBu)-Ser(tBu)-
Asp(OtBu)-Val-Ser(tBu)-Ser(tBu)-Tyr(tBu)-Leu-Glu(OtBu)-Gly-
Gln(Trt)-Ala-Ala-Lys(Glu-OtBu-Palmitoyl)-Glu(OtBu)-Phe-Ile-Ala-
Trp(Boc)-Leu-Val-Arg(Pbf)-Gly-Arg(Pbf)-Gly-O-2-CTC

8

TFA:TIS:DODT:Water

-continued (SEQ ID NO: 1)

His-Ala-Glu-Gly-Thr-Phe-Thr-Ser-Asp-Val-Ser-Ser-Tyr-Leu-
Glu-Gly-Gln-Ala-Ala-Lys(Glu-Palmitoyl)-Glu-Phe-Ile-Ala-Trp-
Leu-Val-Arg-Gly-Arg-Gly-OH
Crude Liraglutide

9

2-CTC resin bound protected Fragment (8) was charged into a peptide synthesis flask. The resin was suspended in dichloromethane (DCM) (10 vol) without stirring for 10 min. The resin was added with a mixture of TFA:TIPS:DODT:Water (8.5:0.5:0.5:0.5 vol). The suspension was gently agitated under nitrogen bubbling and mild stirring at 25-30° C. for 3.0 h. The resin was filtered through a sintered funnel. The filtrate was added into a pre-cooled mixture of MTBE at 0-10° C. After complete addition, the reaction mixture was stirred for 1.0 h at 0-35° C. to precipitate an off-white solid. The precipitated solid was then filtered through a Buckner funnel and washed with MTBE. The suction dried solid was then dried in a vacuum oven at 35-40° C. till constant weight.

Step 10: Purification of Crude Liraglutide

Step (10a): Purification-1

3.6 g crude D-liraglutide (9) obtained after global deprotection was dissolved in 300 mL buffer A, pH was adjusted to 8.5-9.5 using ~0.5 mL ammonium hydroxide solution and purification was carried out as per following parameters:

i) Column specification: 250×50 mm SS
ii) Media Specification: C-18 (3rd generation), 10μ, 100 A°
Or C-18 (3rd generation), 10μ, 120 A°
iii) Mobile Phase A: 0.01M ammonium bicarbonate, Mobile Phase B: Acetonitrile,
iv) Gradient program for Material elution: 30 to 45% B Flow rate: 50 to 120 ml/min (150 to 360 cm/Hr linear flow rate)
v) Pooling criteria: Fractions having UPLC purity ≥85% and single maximum impurity ≤3% were pooled for purification 2.
vi) Fractions having UPLC purity ≤85% and ≥60% were pooled for further purification.

Step (10b): Purification-2

Pooled fractions from purification-1 having peptide content 900 mg was further diluted with equal amount of purified water and further purification was carried out as per following parameters:

i) Column specification: 250×50 mm SS
ii) Media Specification: C-18 (3rd generation), 10μ, 100 A°
Or C-18 (3rd generation), 10μ, 120 A°
iii) Mobile Phase A: 0.1% TFA in water, Mobile Phase B: Acetonitrile,
iv) Gradient program for Material elution: 30 to 45% B Flow rate: 50 to 120 ml/min (150 to 360 cm/Hr linear flow rate)
v) Pooling criteria: Fractions having HPLC purity ≥96% and single maximum impurity ≤0.5% were pooled for purification 3.
vi) Fractions having HPLC purity ≤96% and ≥85% were pooled for repurification.

Step (10c): Purification-3

Pooled fractions from purification-2 having peptide content 1200 mg was further diluted with equal amount of purified water and repurification was carried out as per following parameters:

i) Column specification: 250×50 mm SS
ii) Media Specification: C-18 (3rd generation), 10μ, 100 A°
Or C-18 (3rd generation), 10μ, 120 A° iii) Mobile Phase A: 0.05% ammonium hydroxide in water, Mobile Phase B: Acetonitrile, Mobile Phase C: 3% ammonium acetate in water, Mobile Phase D: Purified water iv) Gradient program for Material elution: 20 to 35% B Flow rate: 50 to 120 ml/min (150 to 360 cm/Hr linear flow rate)

v) Pooling criteria: Fractions having HPLC purity ≥98% and single maximum impurity ≤0.3% were pooled for concentration.

vi) Fractions having HPLC purity ≤98% and ≥96% were pooled after repurification.

vii) The pooled fractions from purification-3 were concentrated and subjected to lyophilization to obtain pure liraglutide (I) as off-white to white powder.

viii) Liraglutide obtained had HPLC Purity not less than 99.0% and isolated yield was in the range of 9-12%.

Example 2

Synthesis of D-Liraglutide

D-liraglutide was synthesized as per the following process.

Step 1 to Step 10: The same process described in Example 1 for synthesis of liraglutide was followed for preparation of D-liraglutide except the fragment Fmoc-Ala-OH used in step-6 was replaced with Fmoc-D-Ala-OH. The intermediate compounds include SEQ ID NOs. 8-10.

Example 3

Synthesis of Semaglutide

Semaglutide was synthesized as per the following process.

Step 1 to Step 7: Fragments 1-8 were prepared by using the process described in Example 1 for synthesis of liraglutide.

Step 8: Coupling of Fmoc-PEG2-CH₂—COOH, Fmoc-PEG2-CH₂—COOH, Fmoc-Glu-OtBu and 18-tBu-18-Oxaoctadecanoicacid The coupling was carried out as per the following scheme in stepwise manner:

(SEQ ID NO: 6)

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(NH₂)-Glu(OtBu)-Phe-Ile-Ala-Trp(Boc)-Leu-Val-Arg(Pbf)-Gly-Arg(Pbf)-Gly-O-2-CTC

7

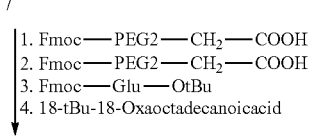

1. Fmoc——PEG2——CH₂——COOH
2. Fmoc——PEG2——CH₂——COOH
3. Fmoc——Glu——OtBu
4. 18-tBu-18-Oxaoctadecanoicacid (SEQ ID NO: 7)

Boc-His(Trt)-Ala-Glu(OtBu)-Gly-Thr(tBu)-Phe-Thr(tBu)-Ser(tBu)-Asp(OtBu)-Val-Ser(tBu)-Ser(tBu)-Tyr(tBu)-Leu-Glu(OtBu)-Gly-Gln(Trt)-Ala-Ala-Lys(Glu-OtBu-Palmitoyl)-Glu(OtBu)-Phe-Ile-Ala-Trp(Boc)-Leu-Val-Arg(Pbf)-Gly-Arg(Pbf)-Gly-O-2-CTC

8

A clear mixture of Fmoc-PEG2-CH₂—COOH (2.0 equiv), N,N-diisopropylcarbodiimide (DIC) (2.0 equiv) and 1-Hydroxybenzotriazole (HOBt) (2.0 equiv) in DMF (10 vol) was added to the resin. The suspension was gently agitated under nitrogen bubbling and mild stirring at 45-55° C. for 30 min. Progress of the reaction was monitored by Kaiser colour test. After completion of the reaction, the reaction solvent was drained and resin washed with DMF (4×10 vol).

Step (8b): Fmoc-Deprotection

The resin was added with a clear mixture of 20% piperidine in DMF lot-1 (10 vol). The suspension was gently agitated under nitrogen bubbling and mild stirring at 25-30° C. for 10 min. The solvent was drained and the resin was added with a clear mixture of 20% piperidine in DMF lot-2 (10 vol). The suspension was stirred at 25-30° C. for 10 min. The solvent was drained and the resin was washed with DMF (2×10 vol) and IPA (1×10 vol) and DMF (2×10 vol). Completion of the Fmoc-deprotection was confirmed by Kaiser colour test.

Step (8c): Coupling of Fmoc-PEG2-CH₂—COOH

A clear mixture of Fmoc-PEG2-CH₂—COOH (2.0 equiv), N,N-diisopropylcarbodiimide (DIC) (2.0 equiv) and 1-Hydroxybenzotriazole (HOBt) (2.0 equiv) in DMF (10 vol) was added to the resin. The suspension was gently agitated under nitrogen bubbling and mild stirring at 45-55° C. for 30 min. Progress of the reaction was monitored by Kaiser colour test. After completion of the reaction, the reaction solvent was drained and resin washed with DMF (4×10 vol).

Step (8d): Fmoc-Deprotection

The resin was added with a clear mixture of 20% piperidine in DMF lot-1 (10 vol). The suspension was gently agitated under nitrogen bubbling and mild stirring at 25-30° C. for 10 min. The solvent was drained and the resin was added with a clear mixture of 20% piperidine in DMF lot-2 (10 vol). The suspension was stirred at 25-30° C. for 10 min. The solvent was drained and the resin was washed with DMF (2×10 vol) and IPA (1×10 vol) and DMF (2×10 vol). Completion of the Fmoc-deprotection was confirmed by Kaiser colour test.

Step (8e): Coupling of Fmoc-Glu-OtBu

A clear mixture of Fmoc-Glu-OtBu (2.0 equiv), N,N-diisopropylcarbodiimide (DIC) (2.0 equiv) and 1-Hydroxy-benzotriazole (HOBt) (2.0 equiv) in DMF (10 vol) was added to the resin. The suspension was gently agitated under nitrogen bubbling and mild stirring at 45-55° C. for 30 min. Progress of the reaction was monitored by Kaiser colour test. After completion of the reaction, the reaction solvent was drained and resin washed with DMF (4×10 vol).

Step (8f): Fmoc-Deprotection

The resin was added with a clear mixture of 20% piperidine in DMF lot-1 (10 vol). The suspension was gently agitated under nitrogen bubbling and mild stirring at 25-30° C. for 10 min. The solvent was drained and the resin was added with a clear mixture of 20% piperidine in DMF lot-2 (10 vol). The suspension was stirred at 25-30° C. for 10 min. The solvent was drained and the resin was washed with DMF (2×10 vol) and IPA (1×10 vol) and DMF (2×10 vol). Completion of the Fmoc-deprotection was confirmed by Kaiser colour test.

Step (8g): Coupling of 18-tBu-18-Oxaoctadecanoicacid

A clear mixture of 18-tBu-18-Oxaoctadecanoicacid (2.0 equiv), N,N-diisopropylcarbodiimide (DIC) (2.0 equiv) and 1-Hydroxybenzotriazole (HOBt) (2.0 equiv) in DMF (10 vol) was added to the resin. The suspension was gently agitated under nitrogen bubbling and mild stirring at 45-55° C. for 30 min. Progress of the reaction was monitored by Kaiser colour test. After completion of the reaction, the reaction solvent was drained and resin washed with DMF (4×10 vol).

Step 9: Preparation of Crude SEMAGLUTIDE (9)

Example 4

(SEQ ID NO: 11)

Boc-His(Trt)-Ala-Glu(OtBu)-Gly-Thr(tBu)-Phe-Thr(tBu)-Ser(tBu)-
Asp(OtBu)-Val-Ser(tBu)-Ser(tBu)-Tyr(tBu)-Leu-Glu(OtBu)-Gly-
Gln(Trt)-Ala-Ala-
Lys[PEG2-PEG2-Glu-OtBu-18-tBu-oxooctadecanoyl]-
Glu(OtBu)-Phe-Ile-Ala-Trp(Boc)-Leu-Val-Arg(Pbf)-Gly-
Arg(Pbf)-Gly-O-2-CTC

8

TFA:TIS:DODT:Water (SEQ ID NO: 3)

His-Ala-Glu-Gly-Thr-Phe-Thr-Ser-Asp-Val-Ser-Ser-Tyr-Leu-Glu-
Gly-Gln-Ala-Ala-Lys[PEG2-PEG2-Glu-18-oxooactadecanoyl]-
Glu-Phe-Ile-Ala-Trp-Leu-Val-Arg-Gly-Arg-Gly-OH
Crude Semaglutide

9

2-CTC resin bound protected Fragment (8) was charged into a peptide synthesis flask. The resin was suspended in dichloromethane (DCM) (10 vol) without stirring for 10 min. The resin was added with a mixture of TFA:TIPS: DODT:Water (8.5:0.5:0.5:0.5 vol). The suspension was gently agitated under nitrogen bubbling and mild stirring at 25-30° C. for 3.0 h. The resin was filtered through a sintered funnel. The filtrate was added into a pre-cooled mixture of MTBE at 0-10° C. After complete addition, the reaction mixture was stirred for 1.0 h at 0-35° C. to precipitate an off-white solid of semaglutide. The precipitated solid was then filtered through a Buckner funnel and washed with MTBE. The suction dried solid was then dried in a vacuum oven at 35-40° C. till constant weight.

Synthesis of D-Semaglutide

Semaglutide was synthesized as per the following process.

Step 1 to Step 10: The same process as described in Example 3 for synthesis of semaglutide was followed for preparation of D-semaglutide except the fragment Fmoc-Ala-OH used in step-6 was replaced with Fmoc-D-Ala-OH. The intermediate compounds include SEQ ID NO. 12.

The foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Advantages of the Present Invention

The present disclosure provides synthetic schemes suitable for preparing different glucagon-like peptide-1 (glp-1) receptor agonists and analogues thereof including liraglutide, D-liraglutide, semaglutide and D-semaglutide.

The present disclosure provides processes for preparing glucagon-like peptide-1 (glp-1) receptor agonists and analogs thereof that can be adapted as economically viable schemes.

The present disclosure provides processes for preparing glucagon-like peptide-1 (glp-1) receptor agonists and analogs and thereof that can be adapted as industrially scalable schemes.

The present disclosure provides processes for preparing glucagon-like peptide-1 (glp-1) receptor agonists and their analogs that are substantially pure.

The present disclosure provides a process for the preparation of glucagon-like peptide-1 (glp-1) receptor agonists and analogue thereof, wherein the use of two dipeptide fragments i.e. Fmoc-Arg(Pbf)-Gly-OH and Fmoc-Glu (OtBu)-Gly-OH helps in reducing the respective Endo-Gly impurities.

We claim:

1. A process for the preparation of liraglutide comprising steps of:

a) anchoring a dipeptide fragment Fmoc-Arg(Pbf)-Gly-OH to a resin and capping it;

b) selectively deprotecting an amino group of the anchored dipeptide fragment;

c) coupling a carboxyl terminus of one more dipeptide fragment Fmoc-Arg(Pbf)-Gly-OH to the fragment of step (b) at N-terminus in the presence of a coupling agent;

d) selectively deprotecting an amino group of the fragment of step (c);

e) coupling a carboxyl terminus of a next N-protected amino acid to the fragment of step (d) in the presence of a coupling agent;

f) repeating steps d) and e) to form a peptide with respective amino acid sequence of liraglutide, Boc-His (Trt)-Ala-Glu(OtBu)-Gly-Thr(tBu)-Phe-Thr(tBu)-Ser (tBu)-Asp(OtBu)-Val-Ser(tBu)-Ser(tBu)    -Tyr(tBu)-Leu-Glu(OtBu)-Gly-Gln(Trt)-Ala-Ala-Lys(Dde)-Glu (OtBu)-Phe-Ile-Ala-Trp(Boc)-Leu-Val-Arg(Pbf)-Gly-Arg (Pbf)-Gly-O-2-resin;

g) removing a lysine side chain protecting group, followed by coupling the peptide fragment of step (f) with Fmoc-Glu-OtBu followed by Fmoc deprotection and coupling of N-terminal peptide attached to resin with palmitic acid;

h) cleaving the peptide from the resin using a mixture of trifluoroacetic acid (TFA):

triisopropylsilane (TIPS): 3,6-dioxa-1,8-octanedithiol (DODT): water to obtain linear crude liraglutide; and i) optionally purifying the crude liraglutide;

wherein the process employs two dipeptide fragments, Fmoc-Arg (Pbf)-Gly-OH and Fmoc-Glu (OtBu)-Gly-OH to obtain step f) sequence.

2. A process for the preparation of liraglutide comprising the steps of:

a) anchoring a dipeptide fragment Fmoc-Arg (Pbf)-Gly-OH to a resin and capping it;

b) selectively deprotecting an amino group of the fragment of step (a);

c) sequential coupling of the dipeptide fragment Fmoc-Arg (Pbf)-Gly-OH, to amino acid fragments Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu (OtBu)-OH, Fmoc-Lys (Dde)-OH, Fmoc-Ala-OH, Fmoc-Ala-OH, Fmoc-Gln(Trt)-OH; dipeptide fragment Fmoc-Glu (OtBu)-Gly-OH, to amino acid fragments Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Phe-OH, Fmoc-Thr (tBu)-OH; dipeptide fragment Fmoc-Glu(OtBu)-Gly-OH, to amino acid fragments Fmoc-Ala-OH and Boc-His(Trt)-OH in the presence of a coupling agent to obtain an a amino acid sequence of Boc-His(Trt)-Ala-Glu(OtBu)-Gly-Thr(tBu)-Phe-Thr(tBu)-Ser(tBu)-Asp (OtBu)    -Val-Ser(tBu)-Ser(tBu)-Tyr(tBu)-Leu-Glu (OtBu)-Gly-Gln(Trt)-Ala-Ala-Lys(Dde)   -Glu(OtBu)-Phe-Ile-Ala-Trp(Boc)-Leu-Val-Arg(Pbf)-Gly-Arg (Pbf)-Gly-O-2-resin;

d) removing a lysine side chain protecting group, followed by coupling the peptide fragment of step (c) with Fmoc-Glu-OtBu followed by Fmoc deprotection and coupling of N-terminal peptide attached to resin with palmitic acid;

e) cleaving the peptide from the resin using a mixture of trifluoroacetic acid (TFA):

triisopropylsilane (TIPS): 3,6-dioxa-1,8-octanedithiol (DODT): water to obtain linear crude liraglutide; and f) optionally purifying the crude liraglutide.

3. The process as claimed in claim 1, wherein the coupling agent is selected from 1-Hydroxybenzotriazole (HOBt), N,N- diisopropylcarbodiimide (DIC), Hexafluorophosphate Benzotriazole Tetramethyl Uronium (HBTU), N,N-Diisopropylethylamine (DIPEA), benzotriazol-1-yl-oxy-tris (dimethyl-amino)-phosphonium hexafluorophosphate (BOP), and O-(7-azabenzotriazol-1-yl)-1,1,3,3-tetramethyluronium hexafluorophosphate (HATU).

4. The process as claimed in claim 2, wherein the coupling agent is selected from 1-Hydroxybenzotriazole (HOBt), N,N-diisopropylcarbodiimide (DIC), Hexafluorophosphate Benzotriazole Tetramethyl Uronium (HBTU), N,N-Diisopropylethylamine (DIPEA), benzotriazol-1-yl-oxy-tris (dimethyl-amino)-phosphonium hexafluorophosphate (BOP), and O-(7-azabenzotriazol-1-yl)-1,1,3,3-tetramethyluronium hexafluorophosphate (HATU).

\*   \*   \*   \*   \*